United States Patent [19]
Martin et al.

[11] Patent Number: 5,891,468
[45] Date of Patent: Apr. 6, 1999

[54] FUSOGENIC LIPOSOME COMPOSITIONS AND METHOD

[75] Inventors: Francis J. Martin, San Francisco; Samuel Zalipsky, Redwood City, both of Calif.

[73] Assignee: SEQUUS Pharmaceuticals, Inc., Menlo Park, Calif.

[21] Appl. No.: 949,046

[22] Filed: Oct. 10, 1997

Related U.S. Application Data

[60] Provisional application No. 60/028,269 Oct. 11, 1996.

[51] Int. Cl.$^6$ .................................................. A61K 9/127
[52] U.S. Cl. .............................. 424/450; 436/829; 935/54
[58] Field of Search ........................... 424/450; 436/829; 935/52, 54

[56] References Cited

U.S. PATENT DOCUMENTS

| | | |
|---|---|---|
| 5,013,556 | 5/1991 | Woodle et al. . |
| 5,370,993 | 12/1994 | Tarnowski et al. . |
| 5,395,619 | 3/1995 | Zalipsky .................................. 424/450 |
| 5,620,689 | 4/1997 | Allen ..................................... 424/178.1 |
| 5,631,018 | 5/1997 | Zalipsky .................................. 424/450 |

OTHER PUBLICATIONS

Düzgünes, N. et al., "Fusion of Liposomes Containing a Novel Cationic Lipid, N–[2,3–(Dioleyloxy)propyl]–N,N, N–trimethylammonium: Induction by Multivalent Anions and Asymmetric Fusion with Acidic Phospholipid Vesicles," *Biochemistry.* 28: 9179–9184 (1989).

Kirpotin, D. et al., "Liposomes with Detachable Polymer Coating: Destabilization and Fusion of Dioleoylphosphatidylethanolamine Vesicles Triggered by Cleavage of Surface–Grafted poly(ethylene glycol)," *FEBS Letters.* 388: 115–118 (1996).

Naka, K. et al., "Molecular Harpoons: Membrane–Disrupting Surfactants that Recognize Osmotic Stress," *J Am. Chem. Soc.* 114: 4011–4013 (1992).

Topchieva, I.N. and Efremova, N.V., "Conjugates of Proteins with Block Co–polymers of Ethylene and Propylene Oxides," *Biotechnology and Genetic Engineering Reviews.* 12: 357–382 (1994).

*Primary Examiner*—Gollamudi S. Kishore
*Attorney, Agent, or Firm*—Judy M. Mohr; Peter J. Dehlinger

[57] ABSTRACT

A fusogenic liposome composition for delivering a liposome-entrapped compound into the cytoplasm of a target cell is described. The liposomes have an outer surface coating of chemically releasable hydrophilic polymer chains which shield hydrophobic polymers on the liposome outer surface. Release of the hydrophilic polymer chains exposes the hydrophobic polymers for interaction with outer cell membranes of the target cells to promote fusion of the liposome with the target cells. Also disclosed is a method for using the composition to deliver a compound to target cells, and a method for selecting suitable hydrophobic polymers for use in the composition.

24 Claims, 15 Drawing Sheets

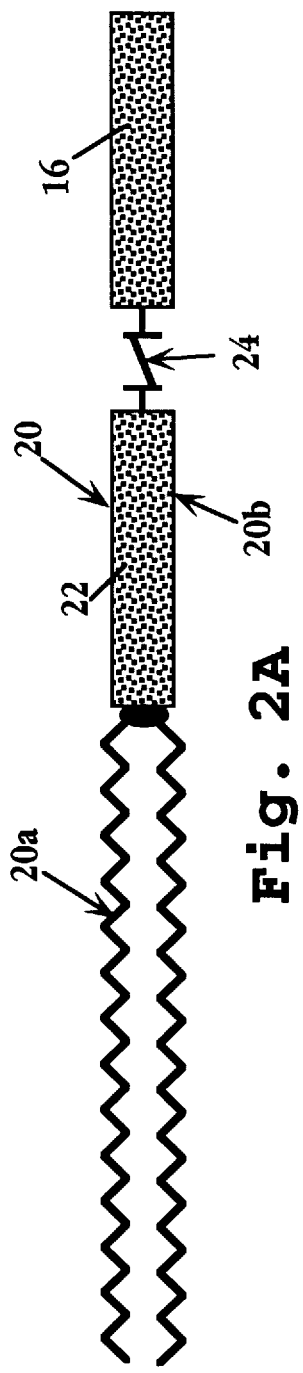
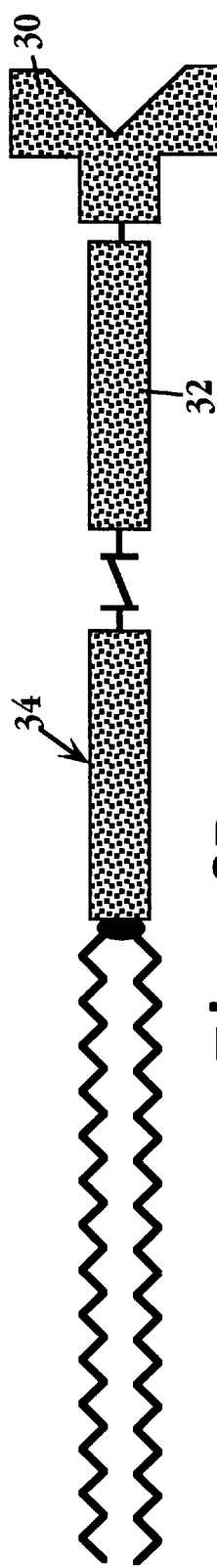
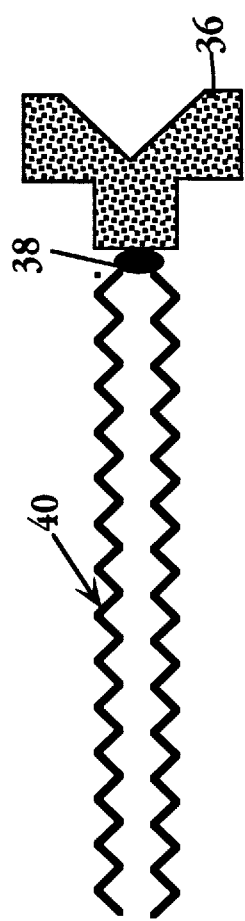
Fig. 2A
Fig. 2B
Fig. 3

FUSOGENIC LIPOSOME COMPOSITIONS AND METHOD

This application claims the benefit of U.S. Provisional Application No. 60/028,269, filed Oct. 11, 1996, incorporated herein by reference in its entirety.

FIELD OF THE INVENTION

The present invention relates to a fusogenic liposome composition for delivery of an agent to the cytoplasmic compartment of a cell, and to methods related thereto.

REFERENCES

Allen, T. M., et al., *Biochemicia et Biophysica Acta* 1237:99–108 (1995).

Beauchamp, C. O., et al., *Annalyt. Biotech.* 131:25 (1983).

DeFrees, S. A., et al., *J. Am. Chem. Soc.*, 118:6101–6104 (1996).

Heath, T. D., *Biochem. et Biophys. Acta*, 640:66 (1981).

Kirpotin, D., et al., *FEBS Letters*, 388:115–118 (1996).

Lee, R. J., et al., *J. Biol. Chem.*, 269(5):3198–3204 (1994).

Martin, F. J., *Biochemistry*, 20:4229 (1981).

Martin, F. J., *J. Biol Chem.*, 257:286 (1982).

Martin, F. J., in SPECIALIZED DRUG DELIVERY SYSTEMS-MANUFACTURING AND PRODUCTION TECHNOLOGY, (P. Tyle, Ed.) Marcel Dekker, New York, pp. 267–316 (1990).

Moore, J. S., and Stupp, S. I., *Macromolecules* 23:65–70 (1985).

Rothberg, K. G., et al., *J. Cell Biol.* 110(3): 637–649 (1990).

Salhany J. M., et al., *The J. Biol. Chem.* 268(11): 7643–7645 (1993).

Still, W. C., et al., *J. Org. Chem.* 43:2923–2925 (1978).

Szoka, F., Jr., et al., *Ann. Rev. Biophys. Bioeng.* 9:467 (1980).

Torchilin and Klibanov, in PHOSPHOLIPID HANDBOOK (Cevic, G., Ed.) Marcel Dekker, NY, 293–321 (1993).

Uster, P. S., et al., *FEBS Letters*, 386:243:246 (1996).

Veronese, F. M., et al., *Appl. Biochem. Biotechnol.* 11:141 (1985).

Zalipsky, S., et al., *Int. J. Peptide Protein Res.* 30:740 (1987).

Zalipsky, S., et al., in POLY (ETHYLENE GLYCOL) CHEMISTRY: BIOTECHNICAL AND BIOMEDICAL APPLICATIONS (J. M. Harris, Ed.) Plenum Press, pg. 347–370 (1992).

Zalipsky, S., *Bioconjugate Chem.*, 4(4):296–299 (1993).

Zalipsky, S., et al., *FEBS Lett.* 353:71–74 (1994).

Zalipsky, S., et al., *Bioconjugate Chemistry*, 705–708 (1995a).

Zalipsky, S., in STEALTH LIPOSOMES (D. Lasic and F. Martin, Eds.) Chapter 9, CRC Press, Boca Raton, Fla. (1995b).

Zhang, Z., et al., *Proc. Natl. Acad. Sci. USA*, 88:10407–10410 (1991).

BACKGROUND OF THE INVENTION

The therapeutic benefit of many compounds is limited by low uptake of the compound by the target cells or by intracellular breakdown of the compound after uptake. Generally, for maximum therapeutic benefit, delivery of the compound to the cytoplasmic compartment of the cell, where translation of mRNA and protein synthesis take place and where there is a direct link to the nucleus, is desired. For many small, uncharged compounds, permeation across the cell membrane may allow relatively efficient uptake by the cell. However, for a variety of larger and/or charged compounds, such as proteins, nucleic acids, and highly water soluble charged organic compounds, passive uptake by permeation across the cell membrane is more limited. Several methods for improving uptake of such compounds into cells have been proposed. For example, a drug can be administered in modified or prodrug form for transport into cells and then undergo enzymatic conversion to an active form within the cells.

Alternatively, the cellular processes of phagocytosis or endocytosis may be used, where drug-containing particles are engulfed by the cells. However, this approach is limited to certain cell types, for example, phagocytosis is limited to cells of monocyte lineage and to certain other myeloid cells, such as neutrophils, and endocytosis is limited to mesenchymal cells, such as vascular endothelial cells and fibroblasts. Another limitation of this approach is that in the normal course of intracellular processing, particles are exposed to the acidic endosome/lysosome compartments and a host of degradative enzymes, including proteases, lipases and nucleases, resulting in degradation of the therapeutic compound, unless an escape from such processing is engineered into the system.

Still another approach to enhancing drug uptake by cells involves the use of fusogenic particles designed to fuse with the surface membrane of a target cell, releasing the particle contents into the cytoplasmic compartment of the cell. Inactivated and reconstituted virus particles have been proposed for this purpose, particularly in gene therapy where large nucleic acid strands are introduced into cells. Virus-like particles composed of fusion-promoting viral proteins embedded in artificial lipid bilayer membranes are another example. However, safety concerns and the expense associated with growing, isolating, and deactivating viral components limit these approaches.

SUMMARY OF THE INVENTION

The invention includes, in one aspect, a liposome composition for fusion with a target membrane of a cell, liposome, or the like. The composition includes a suspension of liposomes designed for targeting to the target membrane. Each liposome contains a therapeutic agent entrapped in the liposomes, an outer liposome surface having a coating of chemically releasable hydrophilic polymer chains, and hydrophobic polymers on the liposome outer surface. The polymers are initially shielded by the hydrophilic polymer coating, then exposed for fusion with the target membrane when the hydrophilic polymer coating is chemically released.

The hydrophilic polymer and hydrophobic polymer preferably form a diblock copolymer in which the two polymer components are joined by a chemically releasable bond, such as a disulfide bond, pH sensitive bond, enzymatically cleavable bond, or photochemically cleavable bond.

Where the liposomes are designed to have an extended blood circulation time, the hydrophilic polymer coating is preferably composed of polymer chains of polyethyleneglycol, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, or polyaspartamide. The polymer chains have a preferred molecular weight of between about 500–10,000 daltons.

The hydrophobic polymer is preferably a chain of polypropylene oxide, polyethylene, polypropylene, polycarbonate, polystyrene, polysulfone, polyphenylene oxide or polytetramethylene ether. The polymer chains have a preferred molecular weight of between 500–3,000 daltons.

More generally, the hydrophobic polymer is preferably a linear polymer effective to cause hemolysis of red blood cells when a water-soluble triblock copolymer containing the hydrophobic polymer and hydrophilic polymer chains joined to opposite ends of the hydrophobic polymer chains by disulfide bonds is incubated with the cells, and the incubate is treated with a reducing agent.

The composition may further include an unshielded ligand attached to the hydrophilic polymer coating, effective for ligand-specific binding to a receptor molecule on a target cell surface prior to chemical release of the hydrophilic polymer coating. As examples, the unshielded ligand may be (i) folate, where the composition is intended for treating tumor cells having cell-surface folate receptors, (ii) pyridoxyl, where the composition is intended for treating virus-infected CD4+ lymphocytes, or (iii) sialyl-Lewis$^x$, where the composition is intended for treating a region of inflammation.

Alternatively, or in addition, the composition may further include a shielded ligand attached to the liposome, effective to bind to target cell surface receptor molecules only after chemical release of the hydrophilic polymer coating.

In a related embodiment, the liposomes contain a shielded cationic lipid effective to impart a positive liposome-surface charge, to enhance binding of liposomes to target cells only after chemical release of the hydrophilic polymer coating.

The agent to be delivered may be a polynucleotide capable of expressing a selected protein, when taken up by a target cell, an oligonucleotide or oligonucleotide analog designed for binding to a specific-sequence nucleic acid in the target cells, or any other therapeutic polymer or small-molecule therapeutic or diagnostic agent.

In another aspect, the invention includes a method of delivering a compound to target cells in a subject, by parenterally administering the above liposome composition to a subject, then contacting the liposomes at the target cells with a cleaving agent effective to release the hydrophilic polymer chains forming the surface coating, to expose hydrophobic polymers on the liposome outer surface for interaction with outer cell membranes of the target cells and thereby promote fusion of the liposomes with the target cells.

In one general embodiment, the hydrophilic polymer chains are releasably attached to the liposome via a reducible chemical linkage, and the contacting step includes administering a reducing agent, such as cysteine, glutathione or ascorbate, to the subject.

In another general embodiment, the hydrophilic polymer chains are releasably attached to the liposomes via a pH sensitive chemical linkage, and the contacting step includes targeting the liposomes to a site, such as a solid-tumor site, having a pH effective to release the chains. For tumor targeting, the liposomes preferably have sizes in the 0.03–0.40 μm for extravasation into a solid tumor region.

Also disclosed is a method for screening a hydrophobic polymer for fusogenic activity with a target membrane, i.e., a hydrophobic polymer suitable for use in the composition of the invention. The method includes adding to a suspension of target cells, a triblock copolymer composed of a segment of the hydrophobic polymer to be tested, and attached to each end of the polymer segment, through a chemically releasable bond, a hydrophilic polymer segment effective to solubilize the hydrophobic polymer segment in the suspension. The suspension is then treated to release the hydrophilic polymers, to expose said hydrophobic segments to said target cells. The suspension of cells, e.g., red blood cells, is then analyzed for lysis, e.g., hemolysis.

These and other objects and features of the invention will be more fully appreciated when the following detailed description of the invention is read in conjunction with the accompanying drawings.

BRIEF DESCRIPTION OF THE DRAWINGS

FIGS. 2A–2B are schematic illustrations of diblock copolymer lipid conjugates useful in the present invention;

FIG. 3 is a schematic illustration of a vesicle-forming lipid with an attached ligand;

DETAILED DESCRIPTION OF THE INVENTION

I. Liposome Composition

The present invention includes a fusogenic liposome composition for fusion with a target membrane. Target membrane, as used herein, refers to a lipid bilayer membrane, for example, a bilayer membrane of a biological cell, a liposome or an artificial planar membrane. In a preferred embodiment, the fusogenic liposome composition of the invention is for use in delivery of a liposome-entrapped compound to the cytoplasmic compartment of a target biological cell.

Figure 1:
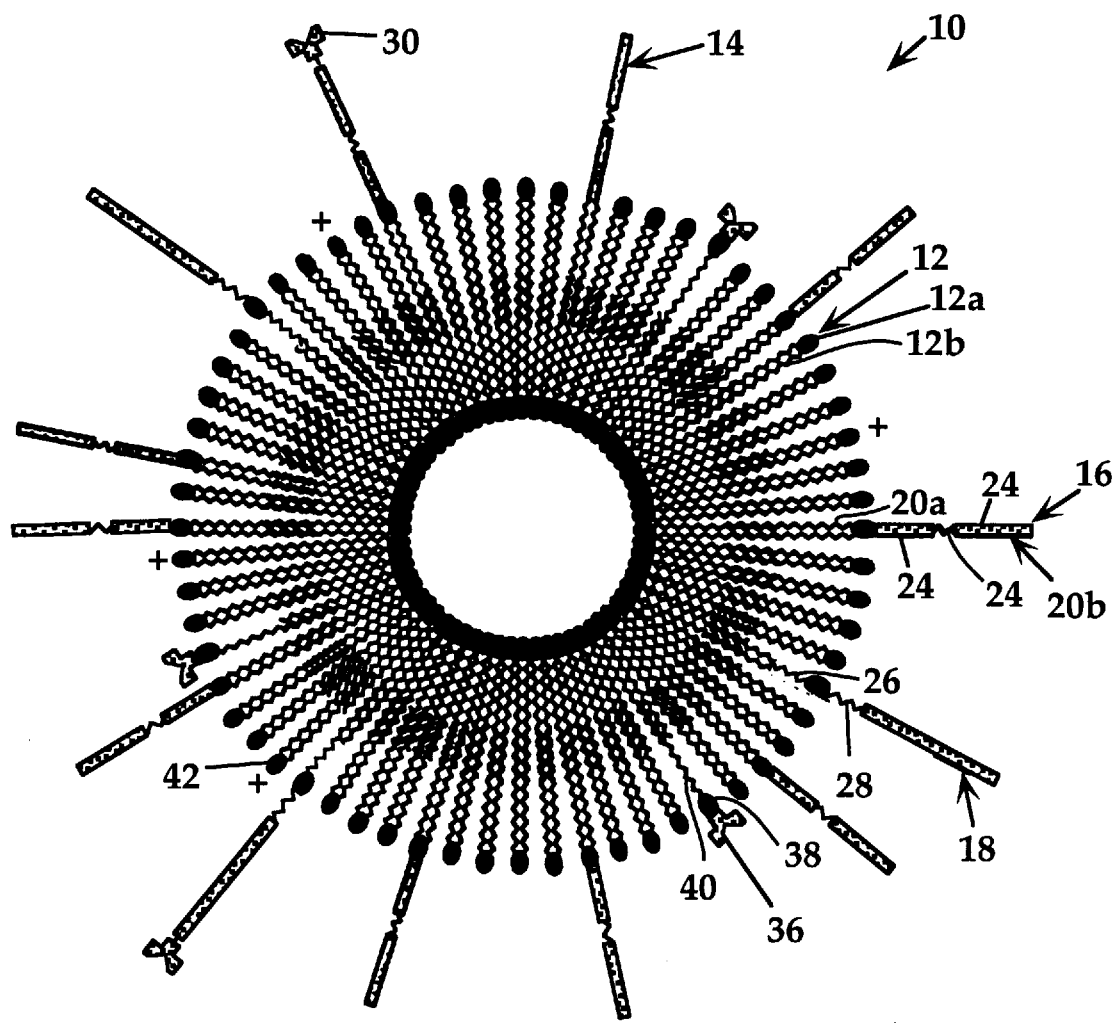
FIG. 1 is a schematic illustration of a liposome prepared in accordance with one embodiment of the invention.

The composition includes liposomes, typically in suspension form, of the type described now with respect to FIG. 1, which shows a representative liposome 10. The liposome is composed of vesicle-forming lipids, such as lipids 12, which each include head groups, such as groups 12a and typically two diacyl hydrophobic lipid chains, such as indicated at 12b. Exemplary liposome-forming lipids are given below.

The liposome has an outer surface coating 14 of hydrophilic polymer chains, such as chains 16, 18, which are preferably densely packed to form a brushlike coating effective to shield liposome surface components, as described below. According to an important feature of the invention, the hydrophilic polymer chains are connected to the liposome lipids, or to hydrophobic chains connected to liposome lipids, by chemically releasable bonds—that is, covalent chemical bonds that can be released by a suitable cleaving agent, such as a reducing agent, a reduced or elevated pH, a hydrolytic enzyme, or a photolytic stimulus, as described further below.

As shown in FIG. 1 and in detail in FIG. 2A, hydrophilic polymer chain 16 forms the distal end of a diblock copolymer lipid conjugate 20 having a vesicle-forming lipid moiety 20a and a diblock copolymer moiety 20b. Diblock copolymer moiety 20b, in turn, consists of a hydrophobic chain 22 which is covalently bound at its proximal end to the polar head group of lipid moiety 20a. Hydrophobic chain 22 is bound at its distal end to hydrophilic polymer chain 16 through a chemically releasable bond 24.

Hydrophilic chain 18, by contrast, is directly linked to the polar head group of a vesicle-forming lipid 26 through a chemically releasably bond 28.

As indicated above, hydrophilic polymer chains, such as such as segment 16 in conjugate 20, are included in liposome 10 as part of the diblock polymer moiety of vesicle-forming lipids on the outer surface of the liposomes. It will be appreciated that the hydrophilic polymer segment in a diblock conjugate functions to enhance the water solubility of the associated hydrophobic chain, to prevent destabilization of the liposome membrane by partitioning of the hydrophobic chains into the liposome bilayer region. As will be discussed below, such destabilization is advantageous in promoting liposome/cell membrane fusion, but is undesirable prior to the fusion event, i.e., during liposome storage, administration and biodistribution to a target site. The types and molecular weights of the hydrophilic and hydrophobic segments suitable for achieving these effects are discussed below.

In addition to their role in "solubilizing" the hydrophobic chains, and shielding them from interactions with other bilayer membranes, the hydrophilic chains also preferably have a surface density sufficient to create a molecular barrier effective to substantially prevent interaction of serum proteins with the liposome surface. As such, the hydrophilic chain coating is effective to extend the circulation time of liposomes in the blood-stream for periods up to several hours to several days.

In the latter embodiment, the hydrophilic chains are preferably present in the outer lipid layer of the liposomes in an amount corresponding to between about 1–20 mole percent of the liposome surface lipids, with lower molecular weight polymers, e.g., 500 daltons, being present at a higher density, e.g., 20 mole percent, and higher molecular weight polymer chains, e.g., 10,000 dalton chains, being present at a lower density, e.g., 1–5 mole percent.

The percent of hydrophobic chains, i.e., the percentage of diblock lipid conjugates in the liposomes, typically ranges between about 5–100% of the total surface lipids containing conjugated hydrophilic polymers. Thus, for example, in a liposome formulation containing 5 mole percent hydrophilic polymer liposome-surface lipids, and 50% diblock lipid conjugates, the hydrophobic polymer would constitute 50%×5%, or 2.5 mole percent, of the surface lipids.

Liposome 10 may further include unshielded surface ligands, such as ligand 30, for targeting the liposomes to a specific target membrane—for example to a specific tissue region or cell type or to a liposome or planar membrane bearing appropriate surface receptor molecules. As seen best in FIG. 2B, ligand molecule 30 is carried at the distal end of a hydrophilic polymer chain 32, such as the chain in a diblock copolymer lipid conjugate 34 of the type described in FIG. 1. Means for conjugating the ligand to the distal end of a hydrophilic polymer chain are well known. The placement of the ligand at or near the distal ends of the polymer chains, i.e., unshielded by the hydrophilic polymer coating, allows the ligand to interact with a target cell containing a ligand-specific surface receptor, prior to removal of the hydrophilic chains from the liposomes.

In addition to the liposome components just described, the liposomes may further include one or more liposome-surface components which are shielded from interaction with target cells until after the removal of the hydrophilic polymers. In one general embodiment, and with reference to FIGS. 1 and 3, the shielded component is a ligand, such as ligand 36, coupled to the polar head group 38 of a vesicle-forming lipid 40. The purpose of the ligand is to bind specifically with a cell receptor after removal of the hydrophilic polymer coating, to force the liposome into proximity with the cell membrane, to enhance the interaction of hydrophobic polymer chains on the liposomes with the target-cell lipid bilayer.

Alternatively, or in addition, the shielded surface component may include vesicle-forming lipids with positively charged polar groups, such as indicated at 42 in FIG. 1. The positive surface charge on the surface of the liposomes is shielded by the hydrophilic coating, during liposome biodistribution to the target site. After removal of the hydrophilic coating, electrostatic interaction between the positive liposome surface charge and the negatively charged target cell acts to draw the liposome into more intimate contact with the cell, to promote fusion mediated by the hydrophobic polymer chains.

Finally, the liposome is prepared to contain one or more therapeutic or diagnostics agents which are to be delivered to the target cell site. As used herein, therapeutic or diagnostic agent, compound and drug are used interchangeably. The agent may be entrapped in the inner aqueous compartment of the liposome or in the lipid bilayer, depending on the nature of the agent. Exemplary therapeutic agents are described below.

A. Vesicle-Forming Lipid Component

The liposome composition of the present invention is composed primarily of vesicle-forming lipids. Such a vesicle-forming lipid is one which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its head group moiety oriented toward the exterior, polar surface of the membrane.

The vesicle-forming lipids of this type are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE), diacylaminopropanediols, such as disteroylaminopropanediol (DS), and phosphatidylglycerol (PG). These lipids are preferred for use as the vesicle-forming lipid, the major liposome component, and for use in the polymer-lipid diblock conjugates and lipids with directly linked hydrophilic polymer chains, which together are preferably included in the liposome outer layer at a mole ratio between about 1–20 mole percent.

Additionally, the vesicle-forming lipid is selected to achieve a specified degree of fluidity or rigidity, to control the stability of the liposome in serum and to control the rate of release of the entrapped agent in the liposome. The rigidity of the liposome, as determined by the vesicle-forming lipid, may also play a role in fusion of the liposome to a target cell, as will be described.

Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

In one embodiment of the invention, the liposomes are prepared with a relatively rigid lipid to impart rigidity to the lipid bilayer. In this embodiment, the lipids forming the liposomes have a phase transition temperature of between about 37°–70° C. In a preferred embodiment, the vesicle forming lipid is distearyl phosphatidylcholine (DSPC), which has a phase transition temperature of 62° C.

In another embodiment of the invention, the lipids forming the bilayer vesicle, i.e., liposome, are effective to impart a positive liposome-surface charge. Such lipids include those typically referred to as cationic lipids, which have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3β[N-(N',N'-dimethylaminoethane) carbamoly] cholesterol (DC-Chol); and dimethyldioctadecylammonium (DDAB).

The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

B. Releasable Polymer Coating

As described above, the hydrophilic polymer coating is formed by including, at least in the outer lipid layer of the liposomes, vesicle-forming lipid conjugates containing a diblock copolymer conjugate of the type shown in FIG. 2A, and optionally, hydrophilic polymers directly linked to the head group of a vesicle-forming lipid, as shown in FIG. 3.

Suitable hydrophilic polymers for use in the conjugates, where the polymers are also intended to extend liposome-circulation time, include polyvinylpyrrolidone, polyvinylmethylether, polymethyloxazoline, polyethyloxazoline, polyhydroxypropyloxazoline, polyhydroxypropyl methacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

In a preferred embodiment, the hydrophilic polymer is polyethyleneglycol, preferably as a PEG chain having a molecular weight between 500–10,000 daltons, typically between 1,000–5,000 daltons.

The surface coating on the liposome provided by the hydrophilic polymer chains provides colloidal stability and, at a sufficient polymer surface density, serves to protect the liposomes from uptake by the reticuloendothelial system, providing an extended blood circulation lifetime for the liposomes to reach the target cells. The extent of enhancement of blood circulation time is preferably severalfold over that achieved in the absence of the polymer coating, as described in co-owned U.S. Pat. No. 5,013,556. Methods for preparing diblock and directly linked lipid-hydrophilic polymer conjugates are discussed below.

C. Hydrophobic Polymer

As described above, the fusogenic liposomes include a hydrophobic polymer for promoting fusion between the liposome and the target cell membrane. The hydrophobic polymer is included in the liposomes as part of the diblock copolymer lipid conjugate, and is directly attached to the head group of a vesicle-forming lipid, such as a diacyl-chain lipid, as will be described below with respect to FIGS. 8–10 (Examples 2–4).

Exemplary hydrophobic polymers suitable for use in the block copolymer of the diblock copolymer-lipid conjugate include polypropylene oxide, polyethylene, polypropylene, polycarbonate, polystyrene, polysulfone, polyphenylene oxide and polytetramethylene ether. Preferably, the hydrophobic polymer has a molecular weight of between 100–5,000 daltons, more preferably between 500–3,000 daltons.

In one preferred embodiment, the hydrophobic polymer is polypropylene oxide (PPO) having a molecular weight between 500–3,000 daltons.

A method for determining hydrophobic polymers and molecular weights suitable for use in the fusogenic liposomes described herein is included in another aspect of the invention. In this method, the fusogenic activity of a selected hydrophobic polymer with a target membrane is determined by attaching a hydrophilic polymer segment to at least one end, and preferably to each end of the hydrophobic polymer. The hydrophilic polymer segments are attached to the hydrophobic segment ends by a releasable linkage, as described below. The tri-block copolymer is added to a suspension of target cells, for example, a suspension of erythrocytes. The hydrophilic polymer segments are released from the hydrophobic segment, by cleavage of the releasable linkage, exposing the hydrophobic segments to the outer membrane of the target cells. The target cells are then analyzed for lysis, e.g., hemolysis of erythrocytes.

Example 1 describes preparation of a tri-block copolymer for determining the fusogenic activity of a hydrophobic polymer. As outlined in Example 1 and shown in FIG. 4, a tri-block copolymer composed of PPO and PEG is prepared by first forming an intermediate mPEG-DTP-OSu (compound III) by reacting methoxypoly(ethylene glycol) amine (compound I) with an excess of dithiobis (succinimidyl propionate) (DTSP, compound II) dissolved in dimethyl formamide (DMF). PPO-diamine (compound IV) is reacted with a slight excess of mPEG-DTP-OSu (compound III) to form a di-PEGylated PPO product (compound V), e.g., mPEG-PPO-mPEG, where the polymer blocks are joined by cleavable disulfide linkages.

This tri-block copolymer was tested for fusion promoting activity, as described in Example 1C, by solubilizing the tri-block copolymer in saline and adding it to a suspension of red blood cells. In a portion of the preparations, dithiothreitol (DTT) was added to reduce the disulfide bonds, releasing the hydrophilic polymer segments and exposing the hydrophobic polymer to the red blood cells. As controls, DTT was not added to some of the preparations and in another preparation, the tri-block copolymer was not added to the cells, however the cells were exposed to DTT. All of the samples were incubated and the hemolytic activity of the PPO was determined by analyzing the supernatant for absorbance at 480 nm and by examining the cells microscopically under phase contrast optics.

Figure 5:
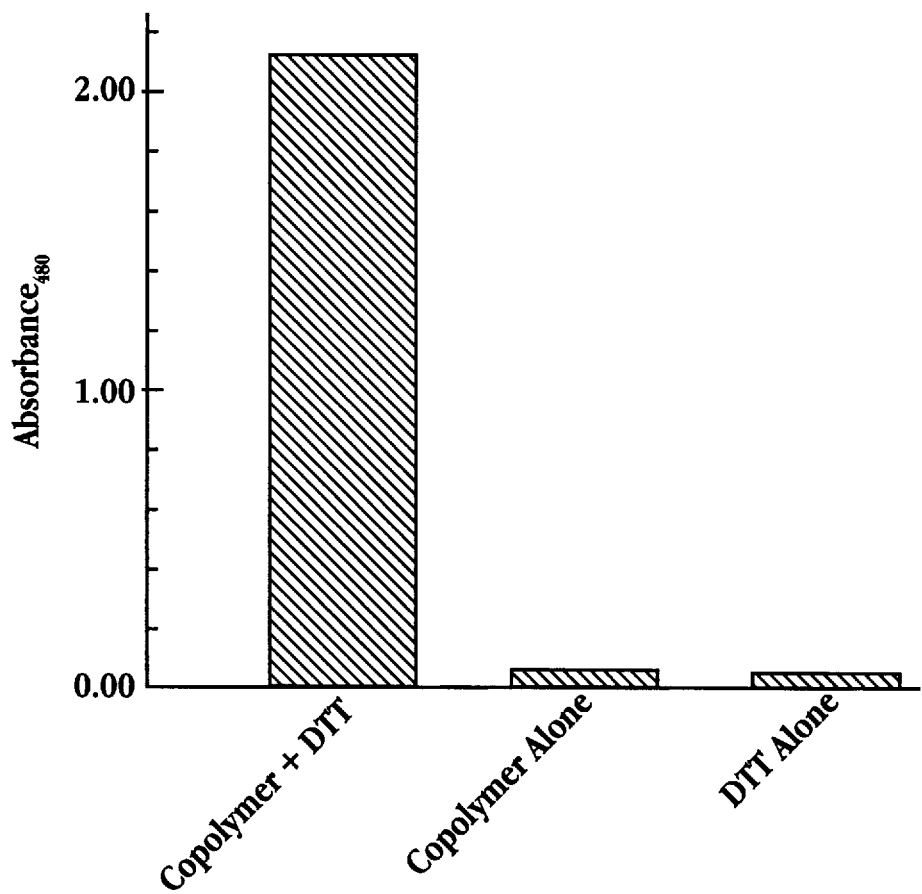
FIG. 5 is a plot showing absorbance at 480 nm of red blood cells exposed to (a) mPEG-PPO-mPEG triblock copolymer with releasable disulfide bonds and the reducing agent dithiothreitol (DTT), (b) mPEG-PPO-mPEG tri-block copolymer alone, and (c) DTT alone.
Figure 6A:
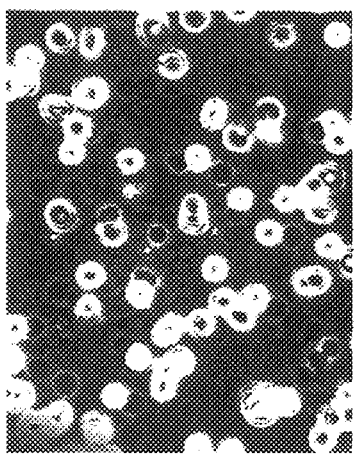
FIGS. 6A–6C are photomicrographs of preparations (a), (b) and (c) in FIG. 5 viewed under phase contrast optics at a magnification of 630×, where FIG. 6A corresponds to the mPEG-PPO-mPEG triblock copolymer and the DTT preparation (a), FIG. 6B corresponds to the mPEG-PPO-mPEG tri-block copolymer alone preparation (b) and FIG. 6C corresponds to the preparation (c) of DTT alone.
Figure 6B:
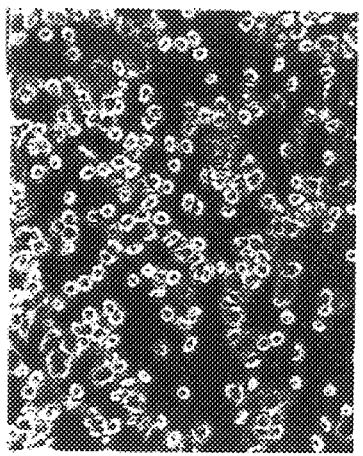

The absorbance values at 480 nm for the preparations containing a tri-block copolymer of 0.78 mg/mL and for the control preparation were measured and are shown in FIG. 5, where bar (a) shows absorbance for the samples containing the tri-block copolymer plus DTT, bar (b) shows absorbance for the samples containing the tri-block copolymer alone and bar (c) shows absorbance for the control preparation (cells plus DTT). Photomicrographs for the three preparations are shown in FIGS. 6A–6C, where FIG. 6A corresponds to bar (a) of FIG. 5, and FIGS. 6B and 6C correspond to bars (b) and (c).

Figure 6C:
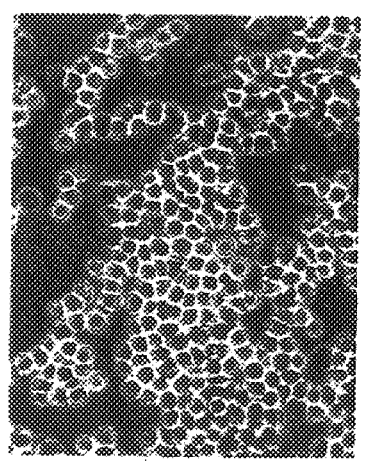

The absorbance data and the photomicrographs indicate that cell lysis is evident only in the preparation containing the tri-block copolymer exposed to DTT, where greater than 80% of the cells lysed, as evidenced by the dark, transparent bodies in the photomicrograph (intact cells are seen as bright bodies in the photomicrographs, see control FIG. 6C). FIG. 6B corresponds to the preparation containing red blood cells incubated with the tri-block copolymer alone without DTT and shows no evidence of cell lysis. FIG. 6C, the preparation of red blood cells in the presence of DTT alone, shows no cell lysis, as evidenced by no effective absorbance and by visually intact cells.

These results indicate that the addition of DTT to the tri-block copolymer cleaved the disulfide bonds between the PEG and PPO liberating free PPO. The free PPO attacked the nearby red cell membranes and led to hemolysis. DTT alone had no effect on the cells and did not induce cell lysis. These results further indicate that $PPO_{2000}$ is effective as a hydrophobic polymer to promote fusion between the liposomes and a cell, and is suitable for use in the diblock copolymer-lipid conjugate of the present invention.

It will be appreciated that the target cells can be biological cells, such as erythrocytes, liposomes or planar artificial membranes. The liposomes can have an encapsulated fluorophore or other material suitable for analysis following lysis of the liposome.

The releasable linkage in the screening method can be a chemically releasable linkage, a pH sensitive linkage, a light sensitive linkage or a heat sensitive linkage. The linkage is cleaved by exposure to the appropriate stimulus, such as a chemical reducing agent, heat, change in pH or light.

It will be appreciated that any hydrophobic polymer, such as those listed above, can be releasably attached to a hydrophilic polymer by suitable end group chemistry. In preferred embodiments, the hydrophobic polymer is a linear polymer segment of polypropylene oxide and the hydrophilic polymer is polyethylene glycol having a molecular weight between 1,000–5,000 daltons.

The activity of hydrophobic polymers and the effect of molecular weight are readily screened by this method. Hydrophobic polymers having high hemolytic activity promote fusion and are suitable for use in the diblock copolymer-lipid conjugate of the invention.

D. Releasable Chemical Linkage

As described above, the liposomes of the present invention include an outer surface coating of releasable hydrophilic polymer chains. That is, the hydrophilic polymer chains are releasably attached to the liposome via a cleavable chemical linkage.

Such chemical linkages include those which can be cleaved under selective physiological conditions, such as in the presence of enzymes or reducing agents. For example, ester or peptide linkages are cleaved by hydrolytic enzymes, such as esterases or peptidases, and disulfide linkages are cleaved by reducing agents such as glutathione, cysteine, or ascorbate normally present in plasma and intracellularly, or these same agents introduced into plasma by, for example, injection. Other releasable linkages include pH sensitive bonds and bonds which are cleaved upon exposure to light or heat.

In one preferred embodiment, the hydrophilic polymer chains are attached to the liposome by a pH sensitive bond, and the liposomes are targeted to a site having a pH effective to cleave the bond and release the hydrophilic chains, such as a tumor region.

Figure 7:
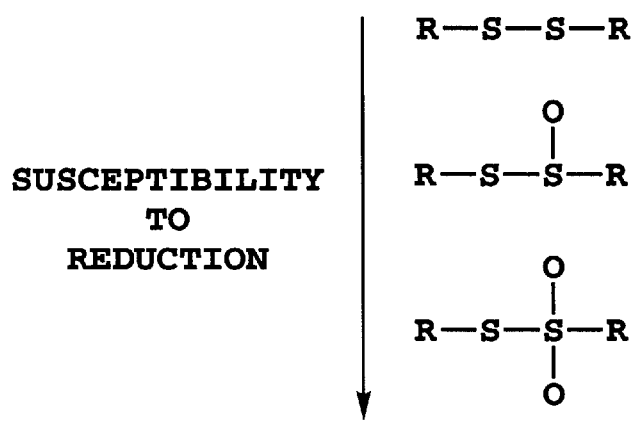
FIG. 7 illustrates several -S-S- linkages and their relative susceptibility to cleavage by a nucleophile.

In another preferred embodiment, the cleavable bond is a disulfide bond, broadly intended herein to refer to sulfur-containing bonds, such as those shown in FIG. 7. The sulfur-containing bonds are synthesized to achieve a selected degree of lability, as indicated in the figure, and include a disulfide bond, a mixed sulfide-sulfone bond and a sulfide-sulfoxide bond. Of the three bonds, the disulfide bond is least susceptible to thiolysis and the sulfide-sulfone (thiosulfonate linkage) bond most susceptible.

Such bonds are useful to tailor the rate of release of the hydrophilic polymer segment from the liposome surface. For example, a very labile disulfide bond is preferred for liposome targeting to blood cells or endothelial cells, since these cells are readily accessible and a shorter liposome blood circulation lifetime is needed. At the other extreme, a long-lasting or hearty disulfide bond is preferred when the liposomal target is tumor tissue, sites of inflammation or infection, skin or other organs, and peripheral lymphatic tissues. In these cases, a longer liposome blood circulation lifetime is generally needed for the liposomes to reach the desired target.

The cleavable bond attaching the hydrophilic polymer chains to the liposome is cleaved in vivo typically as a result of change in environment, such as when the liposomes reach a specific site with a slightly lower pH, such as a region of tumor tissue, or a site with reducing conditions, such as a hypoxic tumor. Reducing conditions in vivo can also be effected by administration of a reducing agent, such as ascorbate, cysteine or glutathione. The cleavable bond may also be broken in response to an external stimuli, such as light or heat.

In studies performed in support of the present invention, described below, liposomes having a releasable surface coating of polyethylene glycol were prepared, where the polyethylene glycol chains were attached to the liposome by a labile, disulfide bond. The liposomes were administered to mice along with a reducing agent to effect release of the polymer chains. Tissue analysis of the mice lung and liver indicates that the hydrophilic polymer coating are released to achieve retention of the liposomes in these organs.

E. Ligand Molecules

As noted above, the liposomes of the invention may include an unshielded (surface-exposed) ligand effective to bind to specific cell surface receptors on the target cell membrane. The ligand molecules are carried on hydrophilic polymer chains which are anchored to the liposome by covalent attachment to a diacyl lipid. The hydrophilic polymer chains may be covalently attached to a liposome-bound lipid through a conventional bond, e.g. irreversibly attached, or through a chemically releasable bond, such as those described above.

Examples of ligands suitable for use in targeting the liposomes of the present invention to specific cell types are listed in Table 1.

TABLE 1

LIGAND-RECEPTOR PAIRS AND ASSOCIATED TARGET CELL

| LIGAND | RECEPTOR | CELL TYPE |
| --- | --- | --- |
| folate | folate receptor | epithelial carcinomas, bone marrow stem cells |
| water soluble vitamins | vitamin receptor | various cells |
| pyridoxyl phosphate | CD4 | CD4 + lymphocytes |
| apolipoproteins | LDL | liver hepatocytes, vascular endothelial cells |
| insulin | insulin receptor | |
| transferrin | transferrin receptor | endothelial cells (brain) |
| galactose | asialoglycoprotein receptor | liver hepatocytes |
| sialyl-Lewis$^x$ | E, P selectin | activated endothelial cells |
| Mac-1 | L selectin | neutrophils, leukocytes |
| VEGF | Flk-1,2 | tumor epithelial cells |
| basic FGF | FGF receptor | tumor epithelial cells |
| EGF | EGF receptor | epithelial cells |
| VCAM-1 | $\alpha_4\beta_1$ integrin | vascular endothelial cells |
| ICAM-1 | $\alpha_L\beta_2$ integrin | vascular endothelial cells |
| PECAM-1/CD31 | $\alpha_v\beta_3$ integrin | vascular endothelial cells |
| fibronectin | $\alpha_v\beta_3$ integrin | activated platelets |
| osteopontin | $\alpha_v\beta_1$ and $\alpha_v\beta_5$ integrins | endothelial cells and smooth muscle cells in atherosclerotic plaques |
| RGD sequences of matrix proteins | $\alpha_v\beta_3$ integrin | tumor endothelial cells, vascular smooth muscle cells |
| HIV GP 120/41 or GP120 C4 domain | CD4 | CD4 + lymphocytes |
| peptomers HIV/GP 120/41 (T cell tropic isolates) or SDF-1 chemokines | fusin | CD4 + lymphocytes |
| HIV GP120/41 (Macrophage tropic isolates) | Chemokine receptor CC-CRK-5 | macrophages, dendritic cells |
| Anti-cell surface receptor antibodies (or fragments thereof) | cell surface receptors | erythrocytes, platelets |
| Anti-cell surface receptor antibodies (or fragments thereof) | cell surface receptors such as CD-34 | bone marrow stem cells |

In one embodiment of the invention, a folate ligand is attached to the distal end of a PEG-derivatized vesicle-forming lipid, e.g., DSPE. The folate ligand is effective to bind to folate receptors on epithelial cells for administration of an entrapped therapeutic agent to the target cell, for example, administration of a neoplastic agent for treatment of epithelial carcinomas.

In another embodiment, sialyl-Lewis$^x$ is attached to PEG-DSPE and included in the liposome composition to target the liposomes to sites of inflammation, more specifically to cells expressing ELAM-1. Preparation of sialyl-Lewis$^x$-PEG-DSPE conjugate has been described (DeFrees, et al., 1996).

In another embodiment of the invention, a pyridoxyl ligand, including pyridoxal, pyridoxine, pyridoxamine, pyridoxal 5'-phosphate and N-(4'-pyridoxyl)amines, is attached to a PEG-DSPE conjugate for targeting the liposomes to CD4 receptors. Synthetic reaction schemes for preparing these ligand conjugates are described below.

In another embodiment, the target membrane is a liposome, and various receptors may be incorporated into the target liposome for fusion with the liposomes of the current invention.

II. Liposome Preparation

A. Preparation of Releasable Polymer Coating

As described above, liposomes in the composition of the present invention include a chemically releasable coating of hydrophilic polymer chains, where the polymer chains making up the coating are attached by a releasable bond in a diblock copolymer conjugate, and optionally, by a releasable bond formed at the polar end of a vesicle-forming lipid.

In studies performed in support of the invention, diblock copolymer-lipid conjugates were prepared, where the diblock polymer was composed of polypropylene oxide (PPO) and methoxy(polyethylene glycol) (mPEG), linked by an aliphatic disulfide bond, and attached through the PPO block to distearoyl or to distearyl phosphatidylethanolamine (DSPE). Preparation of these conjugates is described in Examples 2 and 3, respectively.

Figure 8:
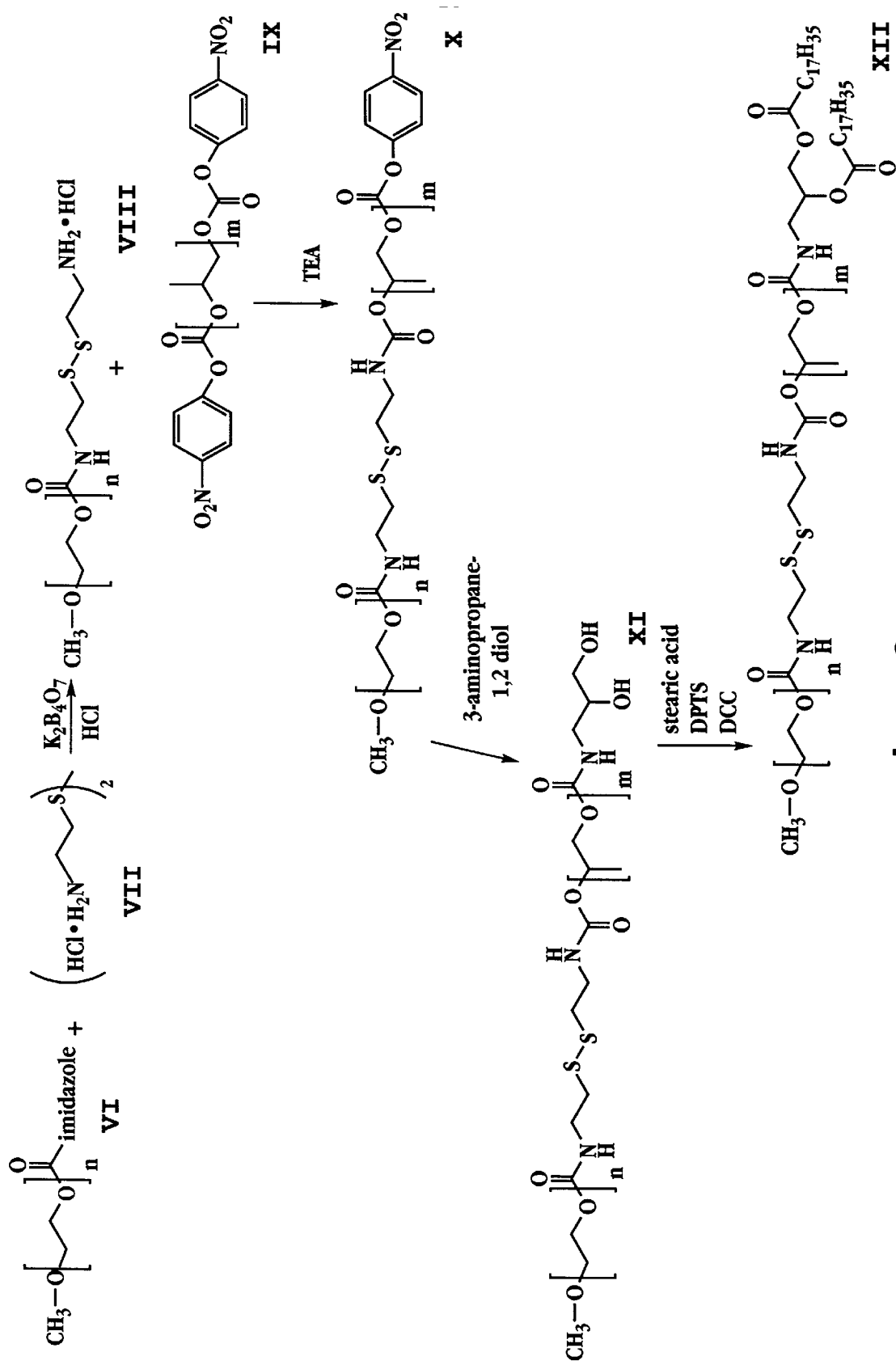
FIG. 8 illustrates a reaction scheme for preparation of a diblock copolymer lipid conjugate of methoxyPEG and PPO covalently linked through a disulfide linkage and attached to a distearoyl lipid anchor.

As set forth in Example 2 and illustrated in FIG. 8, cystamine dihydrochloride (Compound VII), dissolved in potassium tetraborate tetrahydrate, was mixed with α-(imidazol-1-yl)carbonyl-ω-methoxy-poly(ethylene oxide) (Compound VI, prepared as described in Beauchamp, et al., 1983) and the resulting solution was stirred at room temperature for four hours. At this time, the solution was adjusted to pH 1 with 6N HCl and then sodium chloride was added to the saturation limit. The aqueous solution was extracted with chloroform, the organic extracts were combined, dried over magnesium sulfate, and filtered. The solvent was evaporated in vacuo and the resultant colorless gel was dissolved in ethyl acetate. Slow addition of diethyl ether yielded a white precipitate, α[2-aminoethyldithio-N-ethylcarbamoyl-ω-methoxypoly(ethylene oxide) hydrochloride (Compound VIII).

With continuing reference to FIG. 8, α,ω-bis(4-nitrophenoyl carbonate)-poly(propylene oxide) (Compound IX) was prepared as described in Example 2C, and reacted with Compound VIII in the presence of TEA, as described in Example 2D. After a 60 minute reaction time, TLC analysis indicated complete consumption of Compound VIII and, therefore, formation of mPEG-S-S-PPO-nitrophenylcarbonate (Compound X) as a major product and mPEG-S-S-PPO-S-S-mPEG as a minor product. The mixture was treated with aminopropane diol. After further reaction time under nitrogen, the solvent was evaporated and the yellow residue subjected to column chromatography to elute mPEG-S-S-PPO-aminopropane dial (Compound XI).

A solution of compound XI was reacted with stearic acid and 4-(dimethylamino)pyridinium tosylate in dichloromethane in the presence of 1,3-dicyclohexycarbodiimide (DCC). After reaction, filtration and column chromatography, a flocculent white solid, identified as mPEG-S-S-PPO-DS (Compound XII) was obtained. This conjugate is suitable for use in preparing liposomes, as described below, in accordance with the invention.

Figure 9:
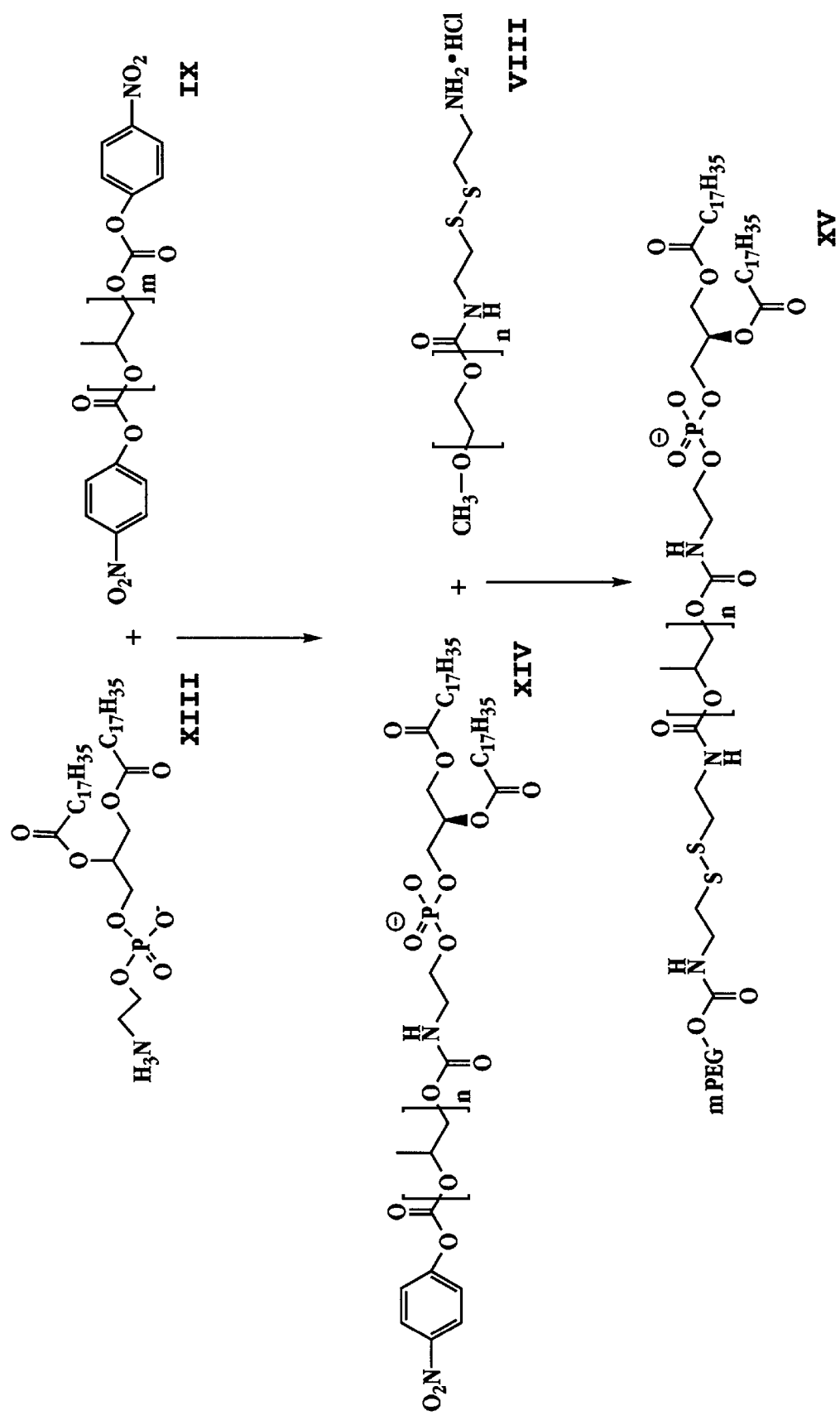
FIG. 9 illustrates a reaction scheme for preparation of a diblock copolymer lipid conjugate of methoxypolyethylene glycol (mPEG) and polypropylene oxide (PPO) covalently linked through a disulfide linkage and attached to the vesicle-forming lipid distearyl phosphatidylethanolamine.

Example 3 describes preparation of a similar diblock-copolymer lipid conjugate, except where the lipid was a vesicle-forming lipid, distearyl phosphatidylethanolamine (DSPE). As illustrated in FIG. 9, DSPE (Compound XIII) was reacted with bis-nitrophenyl carbonate polypropylene oxide (Compound IX, prepared as described in Example 2C) in $CHCl_3$. N-hydroxy-s-norbornene-2,3-dicarboxylic acid imide (HONB) and triethylamine (TEA) were added to the reaction mixture and after further reaction and treatment (detailed in Example 3A) Compound XIV (DSPE-PPO-p-nitrophenyl carbamate) was obtained. Compound VIII (prepared as described in Example 2B) was reacted with Compound XIV in $CHCl_3$ to form the desired mPEG-S-S-PPO-DSPE conjugate, compound XV (Example 3B).

Figure 10A:
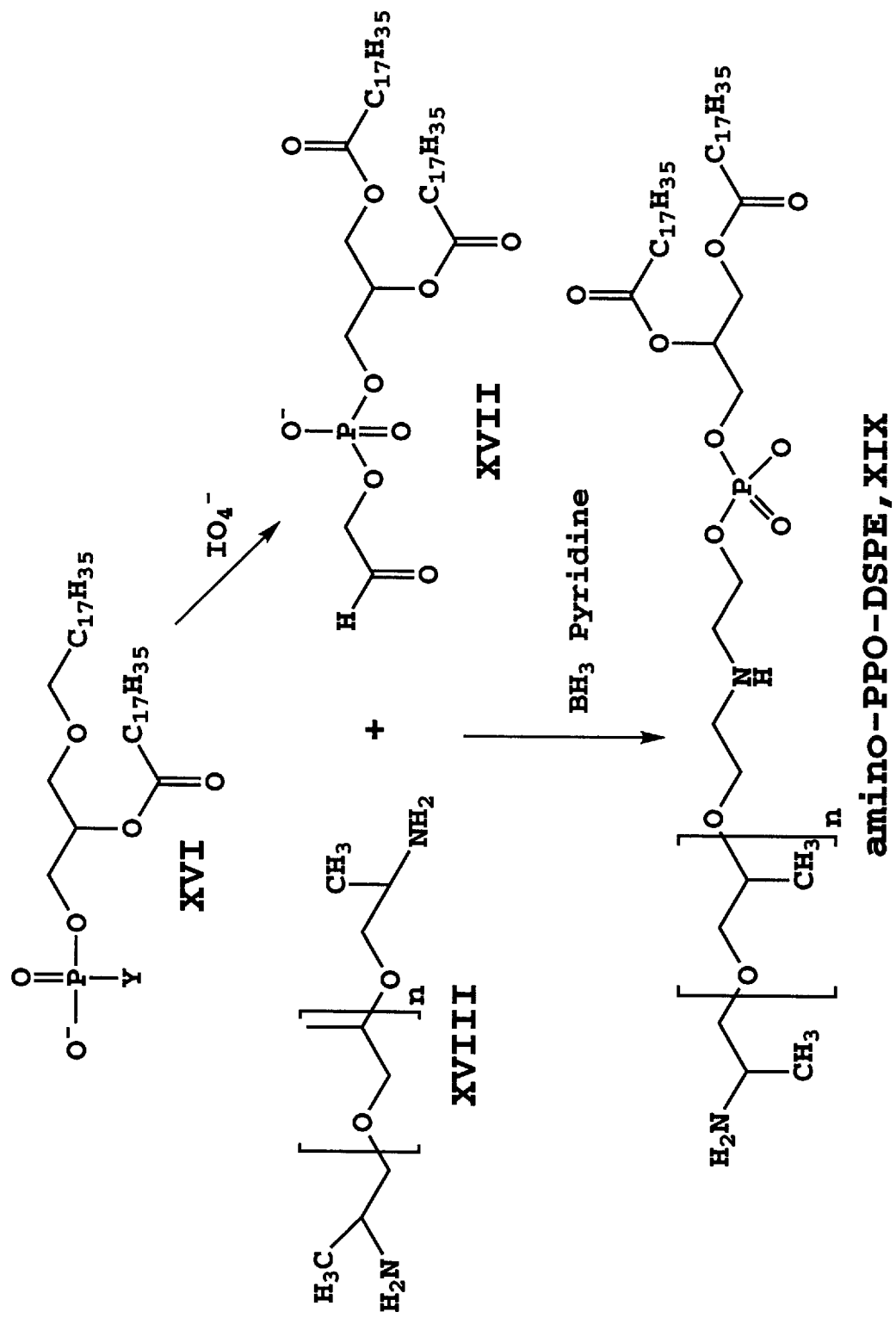
FIGS. 10A–10B show another reaction scheme for preparation of a diblock polymer of mPEG and PPO covalently linked through a disulfide linkage and attached to a diacyl lipid.
Figure 10B:
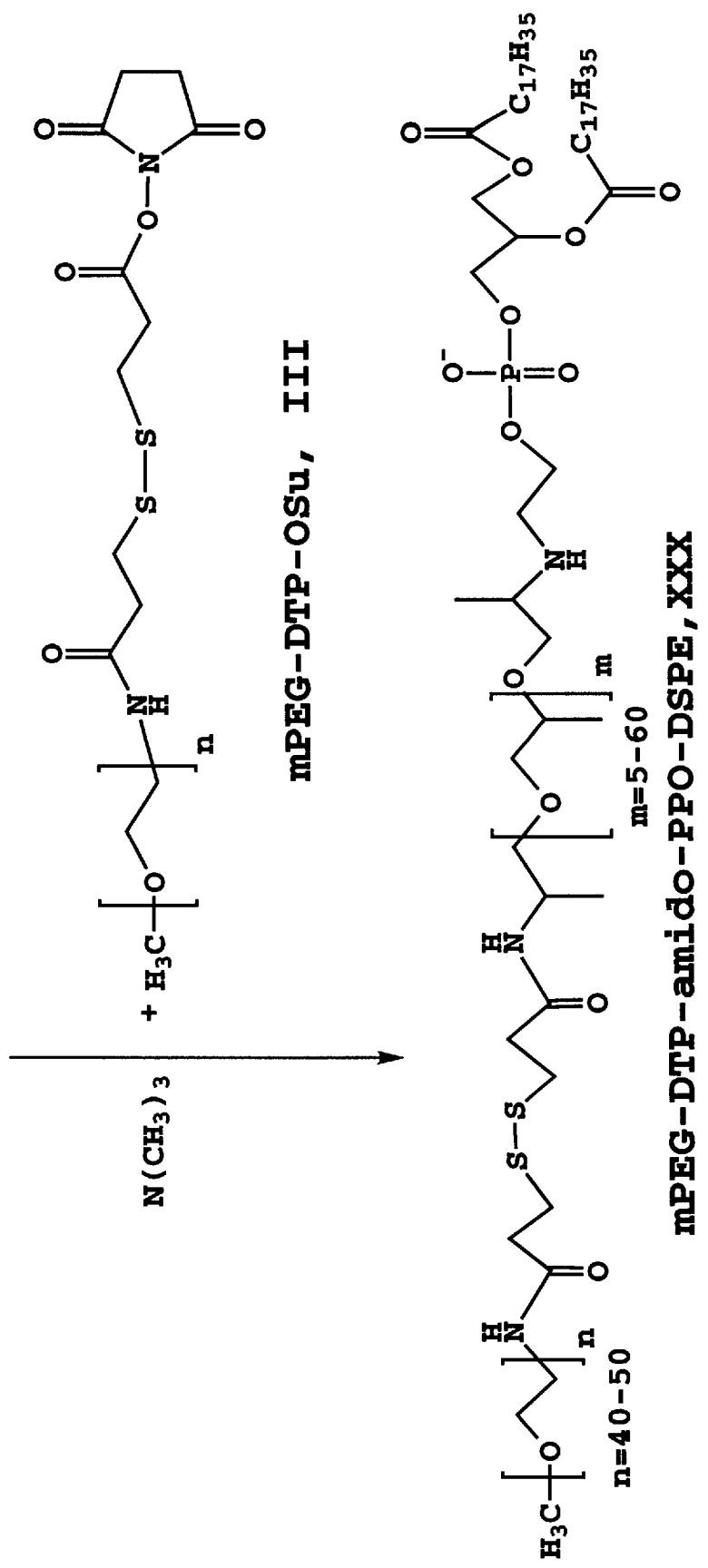

Another reaction scheme for preparation of a mPEG-S-S-PPO-DSPE conjugate is described in Example 4 and illustrated in FIGS. 10A–10B. Here, distearyl phosphatidylglycerol (DSPG, compound XVI) is oxidized with sodium periodate ($NaIO_4$) and then reductively aminated with polypropylene oxide diamine (compound XVIII) to form amino-PPO-DSPE (compound XIX). mPEG-DTP-OSu (compound III), prepared as described in Example 1A, is coupled to amino-PPO-DSPE (compound XIX) to form a diblock copolymer-lipid conjugate, mPEG-DTP-amido-PPO-DSPE (compound XX). Compound XX has a hydrophilic terminal block polymer of PEG and an internal cleavable disulfide linkage to a hydrophobic polypropylene oxide block attached to a terminal lipid, DSPE.

In the examples given above (Examples 2–4), the cleavable bond is a disulfide linkage; however, other linkages are suitable, such as peptide or ester, which can be cleaved under selective physiological conditions, such as in the presence of peptidase or esterase enzymes.

Figure 11:
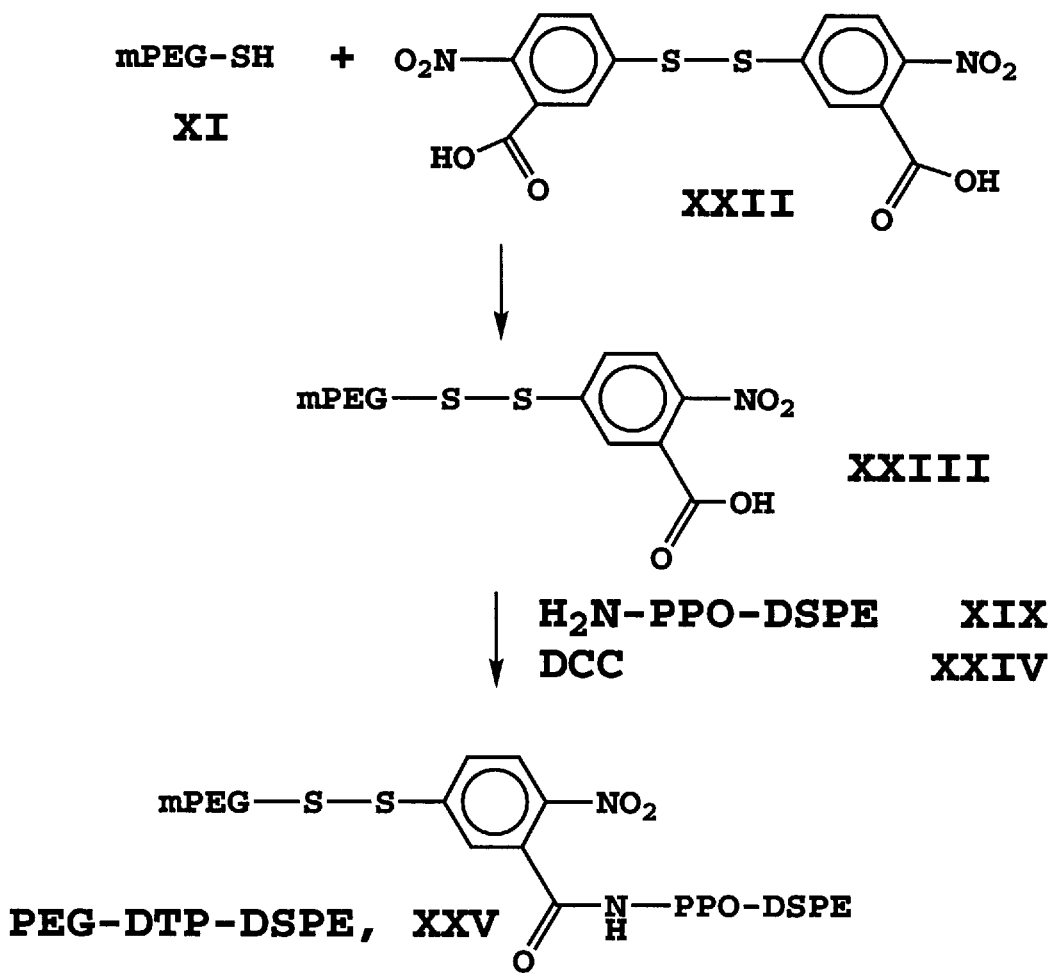
FIG. 11 shows an exemplary labile disulfide bond linking mPEG and PPO polymer segments.

As discussed above, disulfide linkages can be synthesized to vary in susceptibility to reduction, for purposes of tailoring the rate of release of the hydrophilic polymer coating. A reaction scheme for synthesis of a polymer lipid surfactant molecule where the diblock polymer segments (PEG and PPO) are joined by a disulfide bond having increased lability is shown in FIG. 11. mPEG-SH (compound XXI) and Ellman's Reagent (compound XXII) are reacted, as described in Example 5, to form mPEG-3-carboxy-4-nitrophenol disulfide (compound XXIII). This compound is reacted with amino-PPO-DSPE (compound XIX), prepared as described in Example 4A, and with dicyclohexylcarbodiimide (compound XXIV). The diblock copolymer lipid conjugate (compound XXV) has a terminal mPEG segment linked to a PPO segment by a cleavable sulfur-containing linkage which has increased susceptibility to thiolysis. This conjugate (Compound XXV) was used for preparation and in vivo testing of liposomes, as will be described in Example 9.

B. Attachment of a Ligand to Hydrophilic Polymer

As described above, in one embodiment of the invention, the liposomes in the fusogenic composition include a ligand for targeting the liposomes to a selected cell type or another liposome containing the proper receptor. The ligand is bound to the liposome by covalent attachment to the free distal end of a lipid-anchored hydrophilic polymer chain.

In one embodiment of the invention, the hydrophilic polymer chain is PEG, and several methods for attachment of ligands to the distal ends of PEG chains have been described (Allen, et al., 1995; Zalipsky, 1993; Zalipsky, et al., 1994; Zalipsky, et al., 1995a; Zalipsky, 1995b). In these methods, the inert terminal methoxy group of mPEG is replaced with a reactive functionality suitable for conjugation reactions, such as an amino or hydrazide group. The end functionalized PEG is attached to a lipid, typically DSPE. The functionalized PEG-DSPE derivatives are employed in liposome formation and the desired ligand is attached to the reactive end of the PEG chain before or after liposome formation.

Table 1 (discussed above) lists exemplary ligands for use in the liposome composition. By way of example, reaction schemes for attachment of folic acid and pyridoxyl to the distal end of PEG-derivatized DSPE are shown in FIGS. 12A–12B, respectively.

Folic acid (compound XXVI) is a hematopoietic vitamin with a molecular weight of 441 daltons. Folic acid binds to the folate receptor, also known as the membrane folate binding protein, which is a membrane protein having some features of a receptor involved in receptor-mediated endocytosis. The receptor is maximally expressed on the surface of folate-depleted tissue culture cells and is responsible for the high affinity accumulation of 5-methyltetrahydrofolic acid in the cytoplasm of these cells (Rothberg, et al., 1990). It has also been reported that high affinity receptors for folic acid are greatly enriched on certain cancer cells (Lee, et al., 1994). A folic acid ligand incorporated into a liposome by attachment to the distal end of lipidanchored hydrophilic polymer chains, would target the liposomes to such cancerous cells.

Figure 12A:
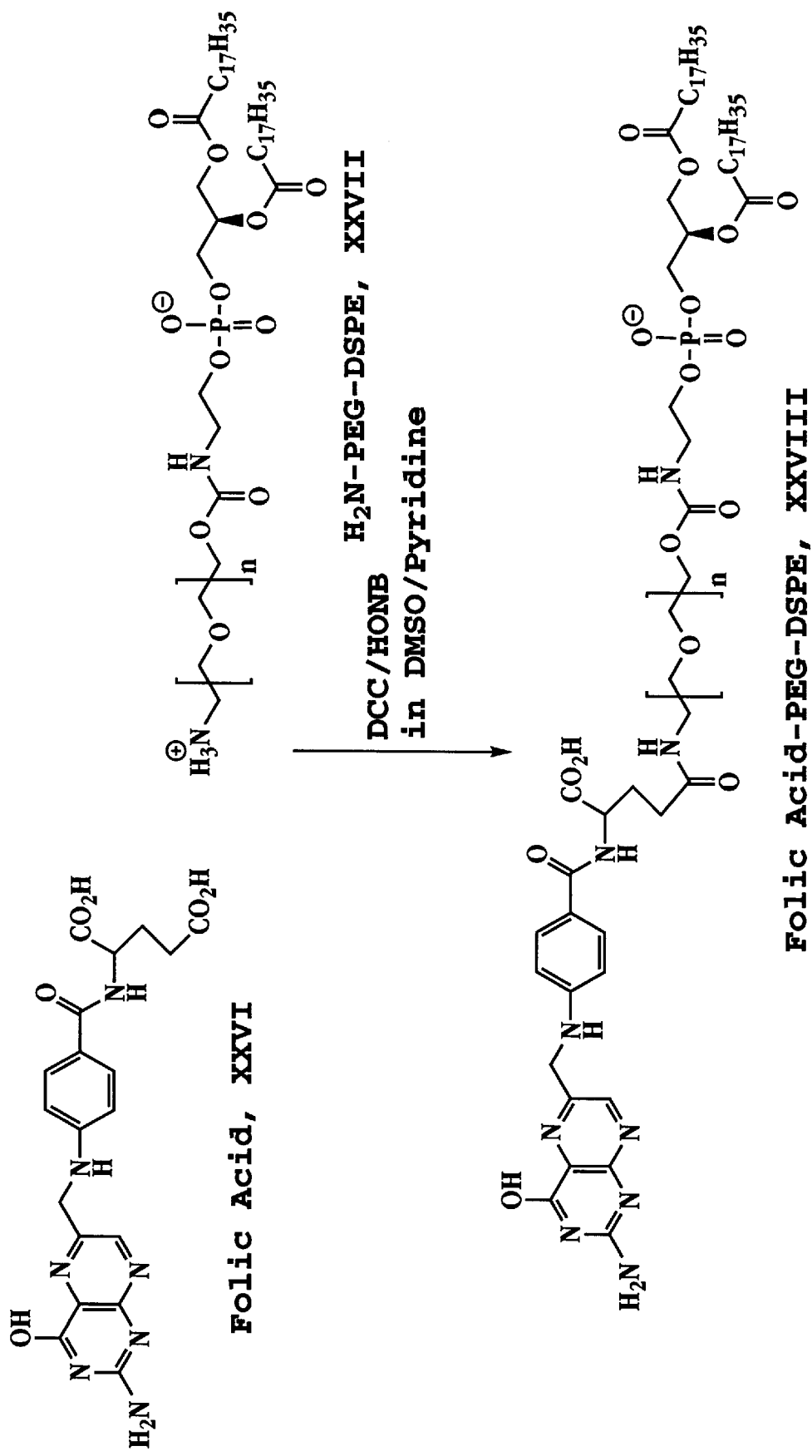
FIGS. 12A–12B show reaction schemes for attachment of folic acid (FIG. 12A) and pyridoxal (FIG. 12B) to end functionalized polyethylene glycol attached to distearyl phosphatidylethanolamine.

Attachment of folic acid to a DSPE-PEG conjugate is described in Example 6 and illustrated in FIG. 12A. Folic acid is mixed with amino-PEG-DSPE (compound XXVII, prepared as described by Zalipsky, et al. (1994)) and reacted in the presence of N-hydroxy-s-norbornene-2,3-dicarboxylic acid imide (HONB) and dicyclohexylcarbodiimide (DCC) to form a folic acid-PEG-DSPE conjugate (compound XXVIII). This conjugate is included in the lipid mixture during liposome preparation to form liposomes including a folic acid targeting ligand.

Figure 12B:
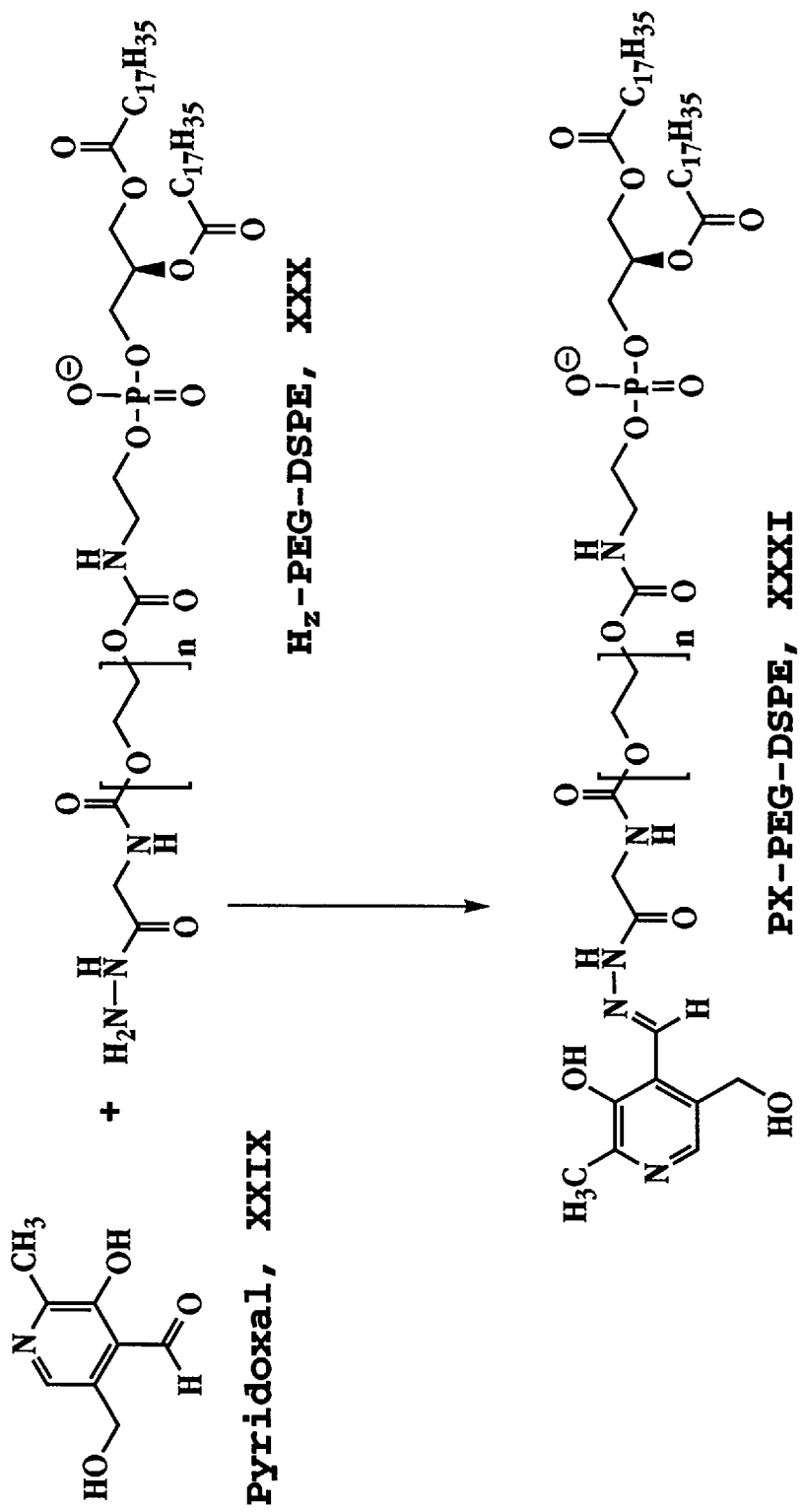

FIG. 12B illustrates attachment of pyridoxal to hydrazide-activated PEG-DSPE. Pyridoxal and related analogues have been studied for use in facilitated transport of biologically active compounds (Zhang, et al., 1991) and for use in AIDS therapy (Salhany, et al., 1993). In AIDS therapy, pyridoxal 5'-phosphate binds to the CD4 protein, the receptor for HIV-1 on T-helper cells. Pyridoxal 5'-phosphate binds tightly to soluble CD4 protein with a stoichiometry of about 1 mol of pyridoxal 5'-phosphate/mol protein. This affinity and targeting to the CD4 protein is useful for targeting liposomes to T cells for AIDS therapy. Attachment of pyridoxal (compound XXIX) to hydrazide activated PEG-DSPE (compound XXX) is described in Example 7 and shown in FIG. 12B.

As another example, the ligand sialyl-Lewis$^x$ is attached to PEG-DSPE and included in the fusogenic liposome composition. Inflammation causes the expression of a polypeptide, endothelial leukocyte adhesion molecule-1 (ELAM-1 or E-selectin), on the surface of endothelial cells of blood vessels, adjacent to sites of inflammation. ELAM-1, in turn, recognizes and binds the polysaccharide moiety sialyl-Lewis$^x$ on surfaces of neutrophils, and recruits neutrophils to sites of inflammation. Sialyl-Lewis$^x$ can be used to target liposomes to cells expressing ELAM-1 for delivery of a therapeutic agent. Preparation of a sialyl-Lewis$^x$-PEG-DSPE derivative has been described (DeFrees, et al., 1996).

As described above with respect to FIG. 1 and FIG. 3, the liposomes optionally contain a ligand bound to the surface of the lipid by attachment to surface lipid components. Such a ligand is initially shielded by the hydrophilic surface coating from interaction with target cells until after the removal of the hydrophilic polymers. Generally, such a ligand is coupled to the polar head group of a vesicle-forming lipid and various methods have been described for attachment of ligands to lipids. In one preferred method, the affinity moiety is coupled to the lipid, by a coupling reaction described below, to form an affinity moiety-lipid conjugate. This conjugate is added to a solution of lipids for formation of liposomes, as will be described. In another method, a vesicle-forming lipid activated for covalent attachment of an affinity moiety is incorporated into liposomes. The formed liposomes are exposed to the affinity moiety to achieve attachment of the affinity moiety to the activated lipids.

A variety of methods are available for preparing a conjugate composed of an affinity moiety and a vesicle-forming lipid. For example, water-soluble, amine-containing affinity moieties can be covalently attached to lipids, such as phosphatidylethanolamine, by reacting the amine-containing moiety with a lipid which has been derivatized to contain an activated ester of N-hydroxysuccinimide.

As another example, biomolecules, and in particular large biomolecules such as proteins, can be coupled to lipids according to reported methods. One method involves Schiff-base formation between an aldehyde group on a lipid, typically a phospholipid, and a primary amino acid on the affinity moiety. The aldehyde group is preferably formed by periodate oxidation of the lipid. The coupling reaction, after removal of the oxidant, is carried out in the presence of a reducing agent, such as dithiothreitol, as described by Heath, (1981). Typical aldehyde-lipid precursors suitable in the method include lactosylceramide, trihexosylceramine, galacto cerebroside, phosphatidylglycerol, phosphatidylinositol and gangliosides.

A second general coupling method is applicable to thiol-containing affinity moieties, and involves formation of a disulfide or thioether bond between a lipid and the affinity moiety. In the disulfide reaction, a lipid amine, such as phosphatidyl-ethanolamine, is modified to contain a pyridylditho derivative which can react with an exposed thiol group in the affinity moiety. Reaction conditions for such a method can be found in Martin (1981). The thioether coupling method, described by Martin (1982), is carried out by forming a sulfhydrylreactive phospholipid, such as N-(4) P-maleimidophenyl (butyryl) phosphatidylethanolamine, and reacting the lipid with the thiol-containing affinity moiety.

Another method for reacting an affinity moiety with a lipid involves reacting the affinity moiety with a lipid which has been derivatized to contain an activated ester of N-hydroxysuccinimide. The reaction is typically carried out in the presence of a mild detergent, such as deoxycholate. Like the reactions described above, this coupling reaction is preferably performed prior to incorporating the lipid into the liposome.

The above-described coupling techniques are exemplary and it will be appreciated that other suitable methods are known in the art and have been described, for example in U.S. Pat. Nos. 4,605,630, 4,731,324, 4,429,008, 4,622,294 and 4,483,929.

C. Liposome Preparation

The liposomes may be prepared by a variety of techniques, such as those detailed in Szoka, et al., 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The lipid components used in forming the fusogenic liposomes of the present invention are preferably present in a molar ratio of about 70–90 percent vesicle-forming lipids, 1–20 percent diblock copolymer lipid conjugate and 0.1–5 percent of a lipid having an attached ligand molecule. As noted above, the hydrophilic polymer added may consist entirely of diblock copolymer lipid conjugate or a combination of diblock copolymer lipid conjugate and polymer directly linked to a lipid. Ideally, the percentage of diblock lipid conjugate in this mixture is the maximum percentage that is consistent with liposome stability. Thus, to optimize the formulation for a particular diblock lipid composition, one would select various ratios of the two types of hydrophilic polymer lipids, and use the highest ratio that gave good liposome stability, as evidenced, for example, by a low rate of leakage of a fluorescent reporter from the liposomes. Preferably, the amount of diblock copolymer lipid conjugate is between 5–100% of the total hydrophilic polymer lipid included in the lipid preparation.

One exemplary formulation includes 80–90 mole percent phosphatidylcholine, 1–20 mole percent of polymer-lipid conjugates, and 0.1–5 mole percent ligand-PEG-DSPE, with the diblock polymer lipid conjugate making up 20–100 percent of the total hydrophilic polymer lipid conjugates. Cholesterol may be included in the formulation at between about 1–50 mole percent. Preparation of an exemplary liposome formulation is described in Example 10.

Another procedure suitable for preparation of the fusogenic liposomes of the present invention involves diffusion of polymer-lipid conjugates into preformed liposomes. In this method, liposomes with an entrapped therapeutic agent are prepared from vesicle-forming lipids. The preformed liposomes are added to a solution containing a concentrated dispersion of micelles of polymer-lipid diblock conjugates and optionally, ligand-PEG-DSPE, and the mixture is incubated under conditions effective to achieve insertion of the micellar lipids into the preformed liposomes. An advantage of this method is that the hydrophobic polymer moiety in the diblock lipid is confined to the outer lipid layer of the liposomes, and is therefore potentially less destabilizing than when the diblock component is incorporated into all of the lipid layers forming the liposomes.

Alternatively, the liposomes may be preformed with the directly linked hydrophilic polymer lipid, and incubated under lipid exchange conditions with the diblock polymer conjugate, to exchange the diblock lipid into the outer liposome layer.

The therapeutic or diagnostic agent to be administered to cells, via cell fusion, in accordance with the invention, may be incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome pH gradient. Other methods, such as reverse evaporation phase liposome preparation, are also available.

The fusogenic liposomes of the invention are preferably prepared to have substantially homogeneous sizes in a selected size range, typically between about 0.01 to 0.5 microns, more preferably between 0.03–0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, 1990).

D. Preparation and In vitro Testing of Fusogenic Activity of Exemplary Liposomes A study was performed in support of the invention to demonstrate that liposomes prepared in accordance with the invention exhibit fusogenic activity following release of the hydrophilic portion of the copolymer-lipid conjugate and exposure of the hydrophobic polymer block. As described in Example 8, liposomes containing entrapped carboxy fluorescein were prepared from the vesicle-forming lipids 1,2-dioleyloxy-3-(trimethylamino) propane (DOTAP), lysophosphatidylcholine and partially hydrogenated soy phosphatidyl choline. The liposomes also included cholesterol and 5 mole percent of the diblock copolymer-lipid conjugate mPEG-S-S-PPO-DS, prepared as described in Example 2 (Compound XII, FIG. 8).

Figure 13:
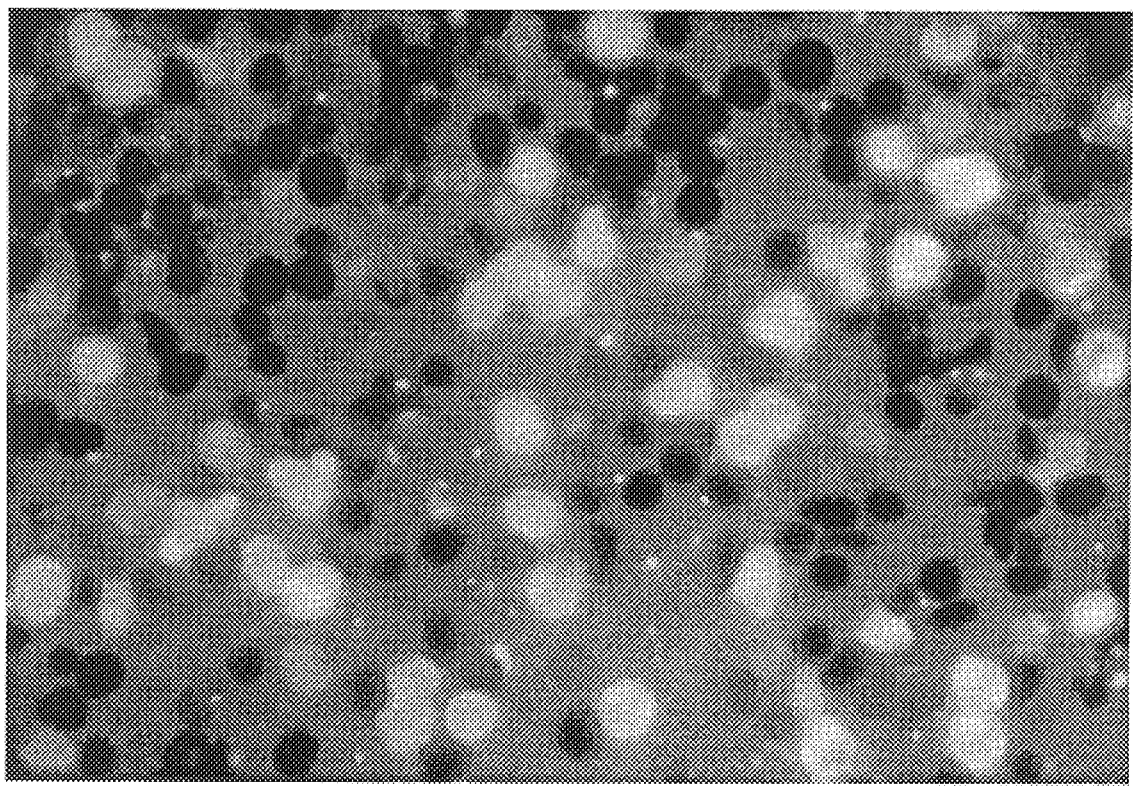
FIG. 13 is a photomicrograph showing fusogenic activity of liposomes prepared in accordance with the invention and containing fluorescein with erythrocyte cells.

The fluorescein-containing liposomes were incubated with resealed human erythrocyte ghosts, prepared as described in Example 8A. The liposomes and ghost cells were centrifuged to ensure contact and then the releasing agent dithiothreitol (DTT) was added to cleave the mPEG block from the mPEG-S-S-PPO-DS conjugate included in the liposomes (Example 8C). After incubation, the cells were resuspended and examined under fluorescence optics, and a photomicrograph is shown in FIG. 13. The erythrocyte ghosts seen in the micrograph exhibit internal fluorescence, indicating that the fluorescein-containing liposomes fused with the cells. Erythrocyte ghost cells which did not fuse with a liposome are also seen in the photomicrograph as darker, transparent cells. Small, fluorescein-containing liposomes are also evident. A control preparation containing erythrocyte ghosts and the same liposome preparation, but which was not exposed to the releasing agent DTT, showed no evidence of liposome-cell fusion, as evidenced by none of the cell ghosts in the optical field under fluorescence optics exhibiting internal fluorescence. In the photomicrograph of FIG. 13, approximately greater than 30% of the erythrocyte ghost cells have internal florescence, indicating fusion with the fusogenic liposomes.

E. Preparation and In vivo Testing of Exemplary Liposomes

Studies were performed in support of the invention using liposomes having a releasable coating of PEG chains by inclusion of compound XXV (FIG. 11) in the liposomes. These liposomes were tested in vivo for release of the PEG chains. As described in Example 9, complexes containing cationic liposomes with the releasable coating of PEG chains and a luciferase-bearing plasmid were prepared. The complexes were prepared by forming a cationic liposome-condensed plasmid complex and incubating the complex with micelles of PEG-DTP-DSPE (compound XXV, FIG. 11) or with micelles of PEG-DSPE (e.g., PEG attached to DSPE by a conventional, non-cleavable bond (Zalipsky 1992a)). The micelles of PEG-DSPE and PEG-DTP-DSPE insert into the cationic liposomes with incubation at room temperature and gentle vortexing for 5 minutes.

Figure 14A:
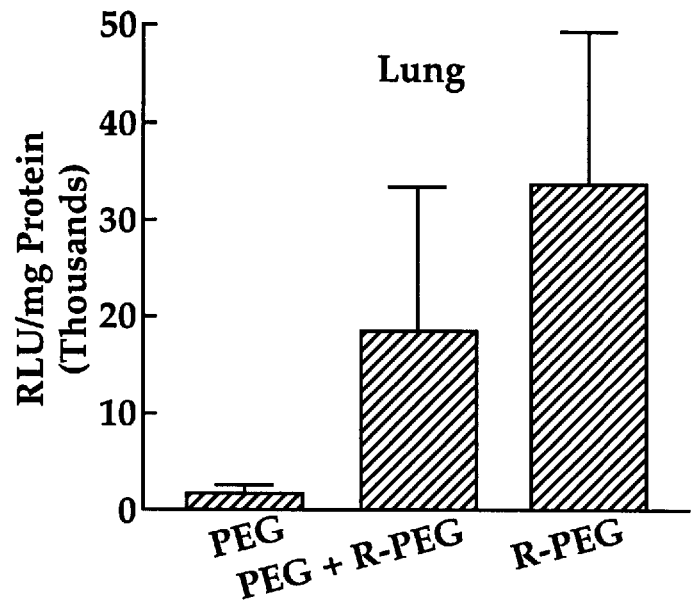
FIGS. 14A–14B are plots of relative luciferase units (RLU) per mg protein in the lung (FIG. 14A) and the liver (FIG. 14B) after in vivo administration to mice of liposome/ plasmid complexes, where the liposomes had an outer surface coating of polyethyleneglycol by including in the liposome 2.5 mole percent of PEG covalently attached to DSPE (PEG), 1 mole percent of PEG covalently attached to DSPE and 1 mole percent of PEG attached to DSPE by a releasable bond (PEG+R-PEG) or 2.5 mole percent of PEG attached to DSPE by a releasable bond (R-PEG).
Figure 14B:
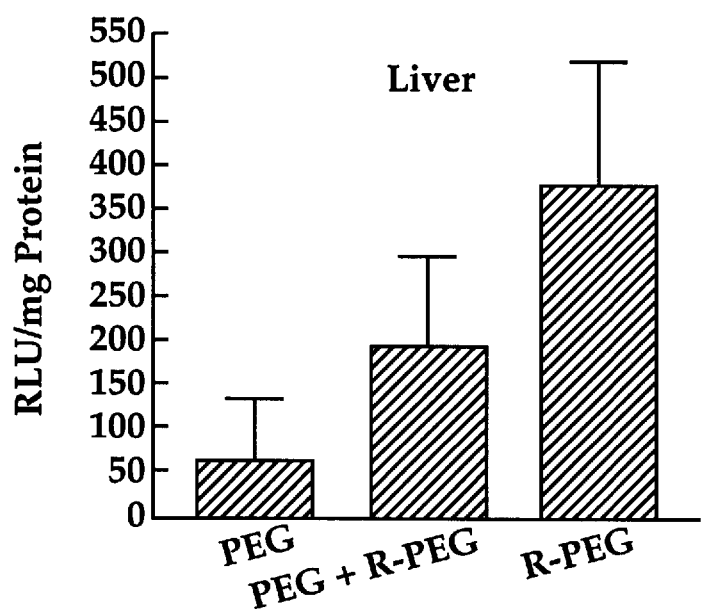

Three liposome formulations were prepared, as described in Example 9. In the first formulation, the PEG coating was not releasable, that is, the PEG was included in the liposomes as PEG irreversibly attached to DSPE. In the second formulation, the liposomes had a PEG surface coating where half of the PEG chains were releasably attached to the liposome surface, and the other half were not releasably attached. In the third formulation, the PEG surface coating on the liposomes was releasable. These formulations are indicated in FIGS. 14A–14B as "PEG", "PEG+R-PEG" and "R-PEG", respectively.

The liposome complexes were administered intravenously to mice. Five minutes after administration, the reducing agent cysteine was added to reduce the disulfide bonds, thereby releasing the releasable PEG from the liposomes. 24 hours after injection, the lung and the liver were analyzed for luciferase activity. The results, shown in FIGS. 14A–14B, show that luciferase activity is higher, e.g., more liposomes are retained in the tissue, for liposomes which have releasable PEG chains. Importantly, the data demonstrates in vivo release of PEG chains by reduction of a releasable linkage. Release of the PEG chains exposes the positive liposome surface charges of the cationic liposomes, enhancing binding to the negative cell membranes and improving retention of the liposomes in the tissues, as evidenced by the higher luciferase activity for the releasable-PEG liposomal formulations.

III. Utility of Fusogenic Liposome Composition

The fusogenic liposome composition described is useful in delivering diagnostic or biologically active therapeutic agents such as drugs, proteins, genetic material or other agents, or receptor molecules, either into a cell membrane, a receptor liposome or the cytoplasm of a cell in vivo or in vitro.

In accordance with the invention, the liposome entrapped agent is delivered directly to the cytosol of the target cell by liposome fusion with the cells, rather than via an endocytotic or phagocytic mechanisms. The liposomes are thus particularly advantageous for delivering therapeutic agents, such as gene constructs, oligonucleotides or oligonucleotide analogs, peptides, proteins, and other biological macromolecules, that do not readily penetrate a cell membrane by passive or active transport.

The fusogenic liposome composition can be administered in vivo by a variety of routes including subcutaneous, intramuscular, interlesional (to tumors), intertracheal by inhalation, topical, internasal, intraocular, via direct injection into organs and intravenous.

A. Administration of Liposome Composition

The fusogenic liposome composition is designed for use in delivering an agent or compound to a target cell, either at an in vivo site or to cultures of cells in vitro. Delivery of the agent is accomplished by fusion of the vesicles with the plasma membrane of the target cells, releasing the agent into the cytoplasmic compartment of the cell. Several applications are discussed below.

1. Delivery of a Therapeutic Agent. A var-iety of therapeutic compounds, including general pharmacologic drugs, peptides and nucleic acids, may have limited therapeutic applications because of the problem of low uptake into target cells. Using the liposome composition of the present invention, entrapped therapeutic compound can be delivered to target cells with high uptake via vesicle-cell fusion.

In this general application, fusogenic liposomes containing encapsulated drug are administered, e.g., intravenously. The fusogenic liposomes, as described above, may include a specific ligand for targeting to cells in need of the entrapped drug. For example, liposomes carrying an anti-tumor drug, such as doxorubicin, can be targeted to the vascular endothelial cells of tumors by including a VEGF ligand in the liposome, for selective attachment to Flk-1,2 receptors expressed on the proliferating tumor endothelial cells. The hydrophilic coating on the liposomes protects the liposomes from uptake by the reticuloendothelial system, providing a long blood circulation lifetime for more effective targeting. At the same time, the ligand, attached to the distal ends of lipid-anchored hydrophilic polymer chains, are exposed for purposes of receptor binding and targeting.

Alternatively, targeting to selected target cells or tissue may be passive, i.e., through the normal biodistribution of liposomes after administration, without the requirement for unshielded ligands. For example, long-circulating liposomes having sizes preferably less than about 0.2 $\mu$m can accumulate, after IV administration, at solid tumor region sites, or sites of inflammation, via extravasation through compromised vasculature.

When the liposomes have reached a selected target site, e.g., by ligand-specific binding of the liposomes to target cells, or accumulation of liposomes in the vicinity of target cells by biodistribution of the injected liposomes, the liposomes are contacted at the target cells with a chemical agent effective to release said chains forming said surface coating. This release exposes the hydrophobic polymers on the liposome surface to the target cells, promoting fusion of the liposomes with the target cell surface as described below.

In one general embodiment, the hydrophilic polymer chains are linked to the hydrophobic chains (or directly to the liposome lipids) via disulfide linkages. In this embodiment, the subject is treated, e.g., by IV administration, of a reducing agent, such as ascorbate, cysteine, or glutathione.

In another embodiment, the chemically releasable linkage may be a pH sensitive bond, where the liposomes are targeted to a region, such as a solid-tumor region, where a typically lower pH can promote hydrophilic polymer fall-off.

Removable of the hydrophilic polymer chains, in whole or in part, exposes the hydrophobic polymer on the liposome surface to the target cell membrane surface. The hydrophobic segment, now in an aqueous environment, will seek a more favorable, e.g., hydrophobic, environment, both in the liposome bilayer and in the adjacent target cell membrane. The partitioning of the hydrophobic chains into target cells will act both to increase the proximity of the liposome to the target cell membrane, and to destabilize the target cell bilayer, making it more susceptible to fusion with the liposome bilayer.

A number of strategies can be employed to optimize or enhance the efficiency of the fusion event.

First, it is desirable to increase the tendency of the exposed hydrophobic chain to partitioning into the target cell bilayer rather than the liposome bilayer. This can be done, in part, by increasing the concentration of high phase transition lipids in the liposomes.

Second, it is desirable to bring the liposomes into close proximity with the target membrane. This may be done, as discussed above, by providing a shielded ligand or positively charged lipid component capable of interacting with the target membrane, after release of the hydrophobic polymers, thus forcing the two bilayers closer together.

Finally, the type and size of the hydrophobic polymer chains can be optimized to enhance fusion efficiency. The method discussed above for examining the ability of hydrophobic polymer chains to lyse erythrocytes can be used to identify optimal polymer size and type.

B. Gene Therapy

Fusogenic liposomes containing an entrapped gene (cDNA plasmid) are delivered to target cells, for ex vivo or in vivo gene therapy. In the latter case, a gene is directly introduced (intravenously, intraperitoneally, aerosol, etc.) into a subject. In ex vivo (or in vitro) gene transfer, the gene is introduced into cells after removal of the cells from specific tissue of an individual. The transfected cells are then introduced back into the subject.

A variety of genes for treatment of various conditions have been described, and coding sequences for specific genes of interest can be retrieved from DNA sequence databanks, such as GenBank or EMBL. The selected coding sequences may encode any of a variety of different types of proteins or polypeptides, depending on the particular application. For example, the fusogenic liposome may be used to introduce sequences encoding enzymes into, e.g., stem cells or lymphocytes of individuals suffering from an enzyme deficiency. For instance, in the case of individuals with adenosine deaminase (ADA) deficiency, sequences encoding ADA may be transfected into stem cells or lymphocytes of such individuals.

In related applications, the liposomes may contain genes encoding any of a variety of circulating proteins, such as $\alpha_1$-antitrypsin, clotting factors (e.g., Factor VIII, Factor IX) and globins (e.g., $\beta$-globin, hemoglobin), for the treatment of hemophilia, sickle-cell anemia and other blood-related diseases. Other examples of gene coding sequences suitable for use with the present invention include sequences encoding structural proteins; receptors, such as low density lipoprotein receptor (LDL-R) for transfection of hepatocytes to treat LDL-deficient patients, human CD4 and soluble forms thereof, and the like; transmembrane proteins such as cystic fibrosis transmembrane conductance regulator (CFTR) for treatment of cystic fibrosis patients; signalling molecules; cytokines, such as various growth factors (e.g., TGF-$\alpha$, TGF-$\beta$, EGF, FGF, IGF, NGF, PDGF, CGF, CSF, SCF), interleukins, interferons, erythropoietin, and the like, as well as receptors for such cytokines; anti-bodies, including chimeric antibodies; genes useful in targeting malignant tumors (e.g., malignant melanoma by transformation of, e.g., tumor-infiltrating lymphocytes, TIL), tumor suppressor genes such as p53 or RB genes that regulate apoptosis such as Bcl–2 gene for thymidine kinase followed by ganciclovir gene for cytosine deaminase followed by 5-fluorocytosine gene for over expression of MDR-1 gene product to protect normal cells from cytotoxic chemotherapy, with genes deleterious to tumors, such as tumor necrosis factor, leukemia inhibitory factor, or various other toxic genes; hormones, such as insulin and growth hormone; transcriptional and translational regulatory elements; and the like. The liposomes may also encode enzymes to convert a non-cytotoxic prodrug into a cytotoxic drug in tumor cells or tumor-adjacent endothelial cells.

In one embodiment of the invention, the liposomes contain a polynucleotide designed to be incorporated into the genome of the target cell or designed for autologous replication within the cell. In another embodiment, the compound entrapped in the lipid vesicles is an oligonucleotide segment designed for sequence-specific binding to cellular RNA or DNA.

Polynucleotides, oligonucleotides, other nucleic acids, such as a DNA plasmid, can be entrapped in the liposome by condensing the nucleic acid in single-molecule form. The nucleic acid is suspended in an aqueous medium containing spermine, spermidine, histone, lysine, mixtures thereof, or other suitable polycationic condensing agent, under conditions effective to condense the nucleic acid into small particles, as described in Example 11. The solution of condensed nucleic acid molecules is used to rehydrate a dried lipid film to form liposomes with the condensed nucleic acid in entrapped form.

C. Use in In Vitro Assays

The fusogenic liposome composition may be targeted to a cell or a target liposome in vitro for use in a homogenous immunoassay format.

In this application, the fusion event introduces an effector molecule carried in the fusogenic liposome into the target cell, e.g., into a biological cell or another liposome. The effector molecule interacts with a compound contained in the target cell to produce a measurable signal.

IV. EXAMPLES

The following examples illustrate methods of preparing, characterizing, and using the fusogenic liposomes of the present invention. The examples are in no way intended to limit the scope of the invention.

EXAMPLE 1

Preparation of Di-PEG-PPO Copolymer for Fusion Activity Screening

A. Preparation of N-succinimidyl-(2-(ω methoxypoly-(oxyethylene)-α-aminocarbonyl)ethyl-diothiopropionate Intermediate, (mPEG-DTP-OSu)

Figure 4:
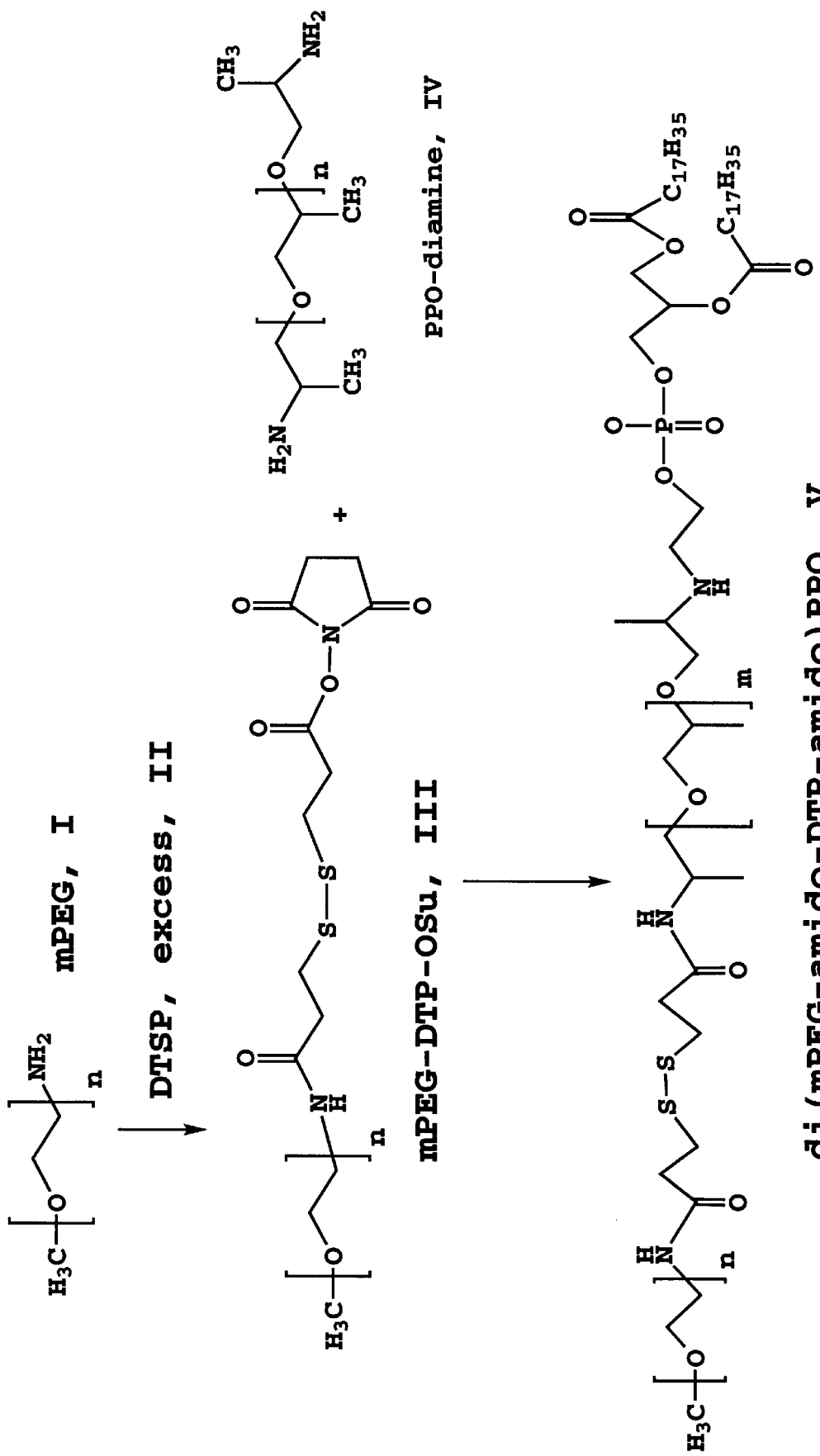
FIG. 4 shows a reaction scheme for preparation of a PEG-PPO-PEG triblock copolymer.

This synthetic scheme is illustrated in FIG. 4. N-succinimidyl-(2-(ω-methoxypoly(oxyethylene)-α-aminocarbonyl)ethyl-diothiopropionate (compound III), is prepared according to the method of Kirpotin, et al., 1996.

A solution of dithiobis(succinimidyl propionate) (873 mg, 2 mmol) (DTSP, compound II), prepared from dithiodipropionic acid (Aldrich, Milwaukee, Wis.), is dissolved in dimethylformamide (10 ml) and treated with methoxypoly (ethylene glycol)amine (2 g, 1 mmol), mPEG-NH$_2$ (compound I), prepared according to the method of Zalipsky (Zalipsky, et al., 1986), and triethylamine (140 ml). The resulting N-succinimidyl ester polymer intermediate, N-succinimidyl-(2-(ω-methoxypoly (oxyethylene)-α-aminocarbonyl)ethyl-diothiopropionate (mPEG-DTP-OSu, compound III) is then purified by recrystallization twice from isopropanol, followed by drying in vacuo over phosphorus pentoxide, to remove residual water. The intermediate is characterized by $^1$H NMR, using deuterated methanol as solvent. $^1$H-NMR (CD$_3$OD): δ 2.6 (m, SCH$_2$CH$_2$CON), 2,85 (s, Su, 4H), 3.0 (overlapping m, SCH$_2$CH$_2$CO$_2$-Su and SCH$_2$CH$_2$CON), 3.38 (s, CH$_3$, #h), 3.64 (s, PEG, ≈180H). The composition of the product mixture, i.e., the relative amount of mono-PEG-ylated (mPEG-DTP-OSu) to di-PEG-ylated dithiodipropionate product (mPEG)$_2$DTP, is determined by comparing the relative integrations of peaks at 2.6 ppm and 2.85 ppm downfield from TMS, assigned to the desired succinate, versus a resonance at 3.0 ppm, assigned to (mPEG)$_2$DTP.

B. Triblock Copolymer Preparation

PPO-diamine, containing two terminal primary amino groups (compound IV), is stirred in methylene chloride until dissolved. To this solution is added a slight excess (1.2 equivalents) of mPEG-DTP-OSu (compound III). The reaction mixture is then stirred for several hours at room temperature. Reaction progress is monitored by TLC; completion is indicated by the disappearance of a spot corresponding to PPO-diamine. The di-PEGylated PPO product, di(mPEG-amido-DTP-amido)PPO (compound V), is purified by column chromatography on silica gel, followed by characterization by $^1$H NMR spectroscopy (CDCl$_3$) to confirm the absence of any remaining mono-PEGylated PPO product.

C. Method of Screening for Fusion Promoting Activity of Hydrophobic Polymers

A tri-block copolymer of PEG$_{2000}$ and PPO$_{2000}$ (Compound V) was prepared by a procedure in accordance with that described above. 50 mg of the tri-block copolymer was dissolved in 1.2 mL phosphate buffered saline (PBS). 0.5 mL was placed in the first two tubes of two rows of 10 tubes each containing 0.5 mL of PBS. Ten serial 2-fold dilutions of the copolymer were made in both rows of tubes. To each of the 20 tubes was added 0.5 mL of a 10% volume/volume suspension of fresh human group O red blood cells (that had been drawn into heparin and washed three times with PBS). A cell control was also prepared by combining 0.5 mL PBS and 0.5 mL of the red cell suspension to a single tube. All the tubes were placed in a refrigerator for 10 minutes after which time 0.1 mL of 0.5M dithiothreitol (DTT) was added to one set of dilutions while 0.1 mL PBS was added to the other set of dilutions. 0.1 mL of DTT was added to the tube containing the cell control. The tubes were placed in the refrigerator for 2 hours. After the incubation, the tubes were placed in a centrifuge and spun at 2000×G for 10 minutes to pellet the cells.

The supernatants were carefully removed and placed in separate tubes. The absorbance values at 480 nm for the supernatants of the 5$^{th}$ dilution (i.e., the tubes containing a concentration of the tri-block copolymer of 0.78 mg/mL) and for the control preparation were measured and are shown in FIG. 5, where bar (a) shows absorbance for the samples containing the tri-block copolymer plus DTT, bar (b) shows absorbance for the samples containing the tri-block copolymer alone and bar (c) shows absorbance for the control preparation (cells plus DTT).

The cells were also examined microscopically under phase contrast optics at a magnification of ×630, and photomicrographs shown in FIGS. 6A–6C. FIG. 6A shows the cell preparation exposed to the tri-block copolymer and to DTT, FIG. 6B corresponds to the cells exposed only to the tri-block copolymer, and FIG. 6C shows the cells exposed to only DTT. As seen, cell lysis is evident only in the preparation containing the tri-block copolymer exposed to DTT, where greater than 80% of the cells lysed, as evident by the dark, transparent bodies in the photomicrograph (intact cells are seen as bright bodies in the photomicrographs).

EXAMPLE 2

Preparation of a Diblock Copolymer-Lipid Coniugate: mPEG-S-S-PPO-DS (Compound XII)

A. Materials and Methods

Materials: Unless otherwise noted, materials were obtained from commercial suppliers and were used as provided. α-(imidazol-1-yl)carbonyl-ω-methoxy-poly(ethylene oxide) was synthesized by known methods (Beauchamp, et al., 1983).

Methods: The phrase "evaporated in vacuo" means the use of a rotary evaporator with a bath temperature not exceeding 40° C. using a water aspirator. Thin-layer chromatography (TLC) was carried out on Analtech 60F-254 silica gel plates, and detection of components on TLC was made by staining with iodine vapor, staining with the Dragendorf reagent (for polyether detection), or by treatment with a cupric sulfate/sulfuric acid solution followed by heating. Solvent systems are expressed as a percentage of the more polar component with respect to total volume (v/v %). Merck grade 9385 silica gel 230–400 mesh (60 Å) was used for chromatography (Merck Sharpe & Dohme, Philadelphia, Pa.), which was carried using the guidelines outlined by Still, et al. (1978). The $^1$H NMR spectra were acquired on 360 MHz GE instrument at Acorn NMR Inc. (Fremont, Calif.) and the chemical shift values are expressed in Δ-values (parts per million) relative to tetramethylsilane as an internal standard. Matrix-assisted laser desorption ionization time of flight mass spectroscopy (MALDI-TOFMS) was obtained with PH-EVANS MALDI triple electrostatic analyzer time-of-flight mass spectrometer at Charles Evans & Associates (Redwood City, Calif.).

B. Preparation of α-[2-Aminoethyldithio-N-ethylcarbamoyl-ω-methoxy-poly(ethylene oxide) Hydrochloride (Compound VIII)

The following reaction is shown in FIG. 8. A 250 mL round-bottom flask was charged with cystamine dihydrochloride (Compound VII, 4.5 g, 20 mmol) dissolved in 50 mL of a 0.01M potassium tetraborate tetrahydrate. To this stirring solution was added, in one portion, α-(imidazol-1-yl)carbonyl-ω-methoxy-poly(ethylene oxide) (Compound VI, n=45) prepared as described in Beauchamp, et al., 1983, and the resultant clear solution was stirred at room temperature for four hours. At this time, the solution was adjusted to pH 1 with 6N HCl and sodium chloride was added to the saturation limit. The aqueous solution was extracted with chloroform (2×75 mL), the organic extracts were combined, dried over magnesium sulfate, and filtered. The solvent was evaporated in vacuo and the resultant colorless gel was dissolved in approximately 70 mL of ethyl acetate. To this clear solution was slowly added 120 mL of diethyl ether to give 1.97 g (88%) of a white precipitate, α-[2-Aminoethyldithio-N-ethylcarbamoyl-ω-methoxy-poly(ethylene oxide) hydrochloride (Compound VIII), that was sufficiently pure for the next reaction. $R_f$=0.49 (2:18:90 water/methanol/chloroform). $^1$H NMR (360 MHz, DMSO-$d_6$) Δ 7.74 (bs, 3), 7.38 (t, 1, J=5.1 Hz), 4.05 (pt, 2, J=4.5 Hz), 3.69 (pt, 1, J=4.7 Hz), 3.50 (bm, ~180), 3.41 (m, 2), 3.23 (s, 3), 3.08 (pt, 2, J=46.7 Hz, 7.1 Hz), 2.90 (pt, 2 J=7.6 Hz), 2.79 (pt, 2, J=6.9 Hz, 6.6 Hz).

C. Preparation of bis p-Nitrophenyl Carbonate Polypropylene (Compound IX)

Polypropylene oxide (PPO, 1 g, 0.5 mmol) was dried azeotropically with benzene. p-Nitrophenyl chlorof ormate (604 mg, 3 mmol, 6 eq) and triethanolamine (TEA, 418 ml, 3 mmol, 6 eq) were added to PPO in $CH_2Cl_2$ (3 ml). After 30 minutes TLC showed that the reaction was complete. The solution was filtered and evaporated to dryness. The crude product was dissolved in $DHCl_3$:$CH_3COCH_3$ (90:10), loaded onto the silica column (the slurry was made with the same solvent), and eluted with the following solvents, $CHCl_3$:$CH_3COCH_3$=90:10 (p-nitrophenyl group eluted), $CHCl_3$:$CH_3COCH_3$=50:50 (product eluted). Appropriate factors were combined, evaporated, and dried in vacuo over $P_2O_5$ to give pure product as clear oil. Yield: 1 g (86%). $^1$H NMR (d6-DMSO): δ 1.05 (d, $CH_3$ $CHCH_2$, 105H); 1.15 (δ, $CH_3$ $CHCH_2$, end 6H); 3.30 (m, $CH_d$$CHCH_2$, 35H); 3.45 (m, $CH_3CHCH_2$, 70H); 4.90 (m, terminal $CH_3CHCH_2$, 2H); 7.50 (d, $NO_2C_6H_4$ PPO, 4H), 8.30 (d, $NO_2C_6H_4$ PPO, 4H)

D. Preparation of mPEG-S-S-PPO-DS (Compound XII)

An oven-dried 25 mL round-bottom flask was charged, under nitrogen, with α,ω-bis(4-nitrophenoyl carbonate)poly(propylene oxide) (Compound IX, m=35, 611 mg, 236 μmol) (prepared as described in Example 2C above, according to the methods of Veronese, et al., 1985) and Compound VIII (512 mg, 230 μmol) in 4.0 mL of dry dimethylformamide. Triethylamine (98 μl, 700 μmol) was then added to this light yellow solution to give a cloudy, bright yellow mixture that was stirred at room temperature under nitrogen for 60 minutes. At this time TLC analysis indicated complete consumption of Compound VIII (and formation of mPEG-S-S-PPO-nitrophenylcarbonate [Compound X, major product] and mPEG-S-S-PPO-S-S-mPEG [minor product]). The reaction was allowed to stir at room temperature under nitrogen for 21 hours. The solvent was then evaporated and the yellow residue subjected to column chromatography ($SiO^2$, 25×150 mm, (1) 10% acetone/chloroform to elute p-nitrophenol then, (2) 5% methanol/chloroform to elute the first mixture, (3) 8% methanol/chloroform) to elute the second mixture containing mPEG-S-S-PPO-aminopropanediol (Compound XI). Solvent evaporation of the appropriate fractions gave 260 mg of an oil that, by TLC analysis, contained two materials of $R_f$=0.58 and $R_f$=0.57 (10% methanol/chloroform) that were positive to iodine staining and polyether-specific Dragendorf staining. This material was used without any further purification. An oven-dried 5 mL flask was charged, under nitrogen, with stearic acid (52 mg, 182 μmol), 4-(dimethylamino) pyridinium tosylate (Moore and Stupp, 1990) (9 mg, 30 μmol), and a solution of Compound XI (260 mg mixture) in 2.0 mL dry dichloromethane. To this clear solution was added 1,3-dicyclohexycarbodiimide (5 mg, 25 μmol) and the reaction was allowed to stir at room temperature under nitrogen. After 30 minutes, a precipitate (1,3-dicyclohexylurea) began to form and TLC analysis showed the formation of a new product spot at $R_f$=0.57 (9% methanol/chloroform, starting material $R_f$=0.49). The reaction was stirred overnight at room temperature under nitrogen. The mixture was filtered through Celite with dichloromethane washes, the solvent was evaporated, and the residue was subjected to column chromatography ($SiO_2$, 25×100 mm, [a] 10–50% gradient of 2-propanol/chloroform, [b] 2:48:50 methanol/2-propanol/chloroform, [c] 5:45:50 methanol/2-propanol/chloroform, [d] 5% methanol/chloroform, [e] 7.5% methanol/chloroform; 100 mL total solvent) to give, following solvent evaporation and lyophilization from 2-methyl-2-propanol/water, 58 mg (10%) of a flocculent white solid, identified as mPEG-S-S-PPO-DS (Compound XII). $^1$H NMR (360 MHz, $CDCl_3$) δ 5.32 (bs, 1), 6.20 (bs, 1), 5.09 (m, 1), 4.91 (bm, 3), 4.28 (dd, 1, J=4.0 Hz, 12.2 Hz), 4.22 (pt, 2, J=4.7 Hz), 4.12 (dd, 1, J=5.6 Hz, 11.8 Hz), 3.83 (m, 1), 3.64 (m, ~180), 3.58–3.51 (bm, ~70), 3.39 (bm, ~35). 3.37 (s, 3), 2.80 (pt, 4, J=6.8 Hz, 5.9 Hz), 2.30 (pt, 4, J=7.4 Hz, 7.5 Hz), 1.61 (bm, 4), 1.32–1.22 (bm, ~62), 1.13 (d, ~99, J=6.9 Hz), 0.88 (t, 6, J=6.6 Hz). MALDI-TOF mass spectrum (DHB, 2,5-dihydroxbenzoate used as matrix material) showed the molecular ion of the conjugate represented by a distribution of lines centered at 4800. The spectrum also showed two distributions representing the fragments of the conjugate generated by cleavage of the disulfide linkage, 2100 and 2700 m/z. The first one composed of spectral lines equally spaced 44 m/z units apart (oxyethylene repeat unit) and the second distribution containing lines equally spaced at 58 units apart (oxypropylene repeat unit).

EXAMPLE 3

Preparation of a Diblock Copolymer-Lipid Conjugate mPEG-S-S-PPO-DSPE (Compound XV)

A. Preparation of DSPE-PPO-p-nitrophenyl carbamate (Compound XIV)

The following reaction is illustrated in FIG. 9. DSPE (Compound XIII, 220 mg, 0.294 mmol) was added to bis-nitrophenyl carbonate polypropylene oxide (Compound IX, 1 g, 0.482 mmol, 3 eq) in $CHCl_3$ (5 ml). N-hydroxy-s-norbornene-2,3-dicarboxylic acid imide (HONB, 79 mg, 0.441 mmol, 1.5 eq) and TEA (304 ml, 2.19 mmol, 7.44 eq) were added to the reaction mixture. The reaction mixture became a yellow cloudy solution. After 4 hours at 42° C. the reaction mixture became clear (yellow). TLC ($CHCl_3$: MeOH: $H_2O$=90:18:2) showed that the reaction went to completion. The product mixture was swirled with Amberlist 15 ion exchange resin (acidic, 1.5 g, 4.6 meq/g) and Amberlist 21 ion exchange (basic, 1.5 g, 4.8 meq/g). Then the product mixture was dissolved in MeOH (3 ml), silica (3 g, Aldrich Chemical Co., Milwaukee, Wis., Silica 60 Å, 230–400 mesh) was added, and was evaporated. The product was eluted by the following solvents, $CHCl_3$:—$CH_3COCH_3$=90:10 (100 ml), $CHCl_3$:iPrOH=98:2 (100 ml), $CHCl_3$:iPrOH=96:4 (100 ml), $CHCl_3$:iPrOH=94:6 (100 ml), $CHCl_3$:iPrOH=92:8 (100 ml), $CHCl_3$:iPrOH=92:8 (100 ml), $CHCl_3$:iPrOH=90:10 (200 ml). Fractions containing pure product were combined and evaporated. t-BuOH (5 ml) was added to the product. The product (Compound XIV) was dried in vacuo over $P_2O_5$ and obtained as white solid (350 mg, 41%). $^1$H NMR ($CDCl_3$): δ 0.88 (m, 6H), 1.15 (s, PPO ($CH_3CHCH_2$), ~105H), 1.26 (s, $CH_2$, 56H), 1.58 (br m, $CH_2CH_2C$=O, 4H) 2.31 (2× t, $CH_2C$=O, 4H), 3.38 (m, PPO ($CH_3CHCH_2$), ~35H), 3.54 (m, PPO ($CH_3CHCH_2$), ~70H), 5.20 (m, $PO_4CH_2CH$, 1H), 7.38 (d, $NO_2C_6H_4$ PPO, 4H), 8.38 (d, $NO_2C_6H_4$ PPO, 4H)

B. Preparation of mPEG-S-S-PPO-DSPE (Compound XV)

With continuing reference to FIG. 9, Compound VIII (Example 2B: mPEG-O(C=O)$NHCH_2CH_2$S-$SCH_2CH_2$—NH2; 56 mg, 0.027 mmol, 1.4 eq), hydroxybenzotriazole (HOBt, 15.2 mg, 0.113 mmol, 6 eq), molecular sieves (50 mg) and TEA (20 ml, 0.143 mmol, 7.7 eq) were added to Compound XIV (DSPE-PPO-p-nitrophenyl carbamate) (55 mg, 0.019 mmol, 1 eq), in $CHCl_3$ (600 ml). After 3 hours TLC ($CHCl_3$: MeOH: IPA=50:1:49) showed the formation of product, but the product spot was very light. Then DMF (0.2 ml) was added to the reaction mixture and stirred at room temperature. After 24 hours the product spot appeared to be darker than the previous day. The product mixture was filtered, lyophilized and then purified by silica gel column chromatography. The product mixture was dissolved in $CH_3COCH_3$:$CHCl_3$ (90:10) and loaded onto the column. The column was eluted with the following solvents: $CHCl_3$:$CH_3COCH_3$=90:10 (50 ml), $CHCl_3$:iPrOH=80:20 (20 ml), $CHCl_3$:iPrOH=60:40 (20 ml), $CHCl_3$:iPrOH: MeOH=50:49:1 (20 ml), $CHCl_3$:iPrOH:MeOH=50:48:2 (20 ml), $CHCl_3$:iPrOH=92:8 (100 ml, $CHCl_3$:iPrOH=92:8 (100 ml), $CHCl_3$:iPrOH=90:10 (200 ml). Fractions containing pure products were combined and evaporated. t-BuOH (5 ml) was added to the product. The product, Compound XV, was dried in vacuo over $P_2O_5$ and obtained as white solid (350 mg, 41%). $^1$H NMR ($CDCl_3$): δ 0.88 (m, 6H), 1.15 (s, $CH_3CHCH_2$, ~105H) 1.26 (s, $CH_2$, 56H), 1.58 br m, $CHCH_2$), ~35H), 3.54 (m, PPO $CH_3CHCH_2$, ~70H), 3.64 (s, PEG, 180H); 5.20 (m, $PO_4CH_2CH$, 1H).

MALDI-TOF mass spectra (DHB matrix) showed the molecular ion of the conjugate represented by a distribution of lines centered at 5000 m/z. The spectrum also showed two distributions representing the fragments of the conjugate generated by cleavage of the disulfide linkage, 2100 and 3000 m/z. The first one composed of spectral lines equally spaced 44 m/z units apart (PEG repeating unit) and the second distribution containing lines equally spaced at 58 units apart (PPO repeating unit).

EXAMPLE 4

Preparation of a Diblock Copolymer-Lipid Conjugate mPEG-DTP-amido-PPO-DSPE (Compound XX)

A. Preparation of a Lipidized Hydrophobic Polymer Intermediate, amino-PPO-DSPE (Compound XIX)

Distearylphosphatidylglycerol (DSPG, compound XVI FIG. 8A) is treated with sodium periodate ($NaIO_4$) as described by Torchilin and Klibanov (1993). The resulting oxidized product, oxidized-DSPE (compound XVII), is then reductively aminated with an excess of polypropylene oxide diamine (diamino-PPO, compound XVIII, n=10–20) (e.g., Jeffamine®, Texaco, Houston, Tex.) in the presence of $NaCNBH_3$, to form the desired amino-linked lipid-functionalized hydrophobic polymer, amino-PPO-DSPE (compound XIX, FIG. 8A).

B. Preparation of a Diblock Copolymer-Lipid Conjugate, mPEG-DTP-amido-PPO-DSPE (Compound XX)

The desired conjugate, mPEG-DTP-amido-PPO-DSPE (compound XX), having a hydrophilic terminal block polymer, PEG, an internal cleavable disulfide bond, and a hydrophobic polypropylene oxide block attached to a terminal lipid, is prepared by coupling the intermediates prepared as described in Examples 1A and 4A above, PEG-DTP-OSu (compound III) and amino-PPO-DSPE (compound XIX) to form the desired copolymer lipid conjugate product, mPEG-DTP-amido-PPO-DSPE (compound XX).

mPEG-DTP-OSu (compound III) is prepared as described above in Example 1A and dissolved in $CHCl_3$. An equimolar amount of amino-PPO-DSPE (compound XIX) is added to the $CHCl_3$ solution of mPEG-DTP-OSu and incubated, in the presence of triethylamine, at 45° C. until clarified. The product (compound XX) is purified as described by Zalipsky, 1993 and the purified product is then characterized by $^1$H NMR. The absence of protons assignable to the reactive succinate group indicate coupling of the two polymer portions to form the desired product. This reaction scheme is summarized in FIGS. 10A–10B.

EXAMPLE 5

Preparation of Copolymer-Lipid Conjugate Linked by a Disulfide Bond Having Increased Lability The preparation of a disulfide interlinked mPEG-PPO-DSPE conjugate containing a modified disulfide linkage having increased susceptibility to cleavage (e.g., thiolysis and/or hydrolysis) is carried out as described below and illustrated in FIG. 11.

Methoxypoly(ethylene glycol) thiol, mPEG-SH (compound XXI), is prepared according to the method of Zalipsky (1987). To a solution of mPEG-SH (compound XXI) in water or dimethylformamide is added an excess of 5'5'-dithiobis(2-nitrobenzoic acid), "Ellman's reagent"

(compound XXII) and the resulting reaction mixture is allowed to stir at room temperature (20°–25° C.). The reaction is monitored by TLC for disappearance of mPEG-thiol starting material, or alternatively, may be followed by IR analysis (S-H stretch) of aliquots of the reaction mixture. The resulting mixed disulfide product, mPEG-3-carboxy-4-nitrophenyl disulfide (compound XXIII), is then recovered by silica gel column chromatography and purified. The resulting disulfide is characterized by $^1$H NMR spectroscopy, and the relative integrations (peak areas) of upfield resonances assignable to the PEG portion of the molecule, and those of peaks corresponding to aromatic protons on the substituted phenyl ring, are compared to determine the extent of di-PEGylated disulfide side product, di(mPEG)disulfide, formed.

The mixed disulfide, mPEG-3-carboxy-4-nitrophenyl disulfide (compound XXIII), is completely dissolved in methylene chloride. To this resulting solution is added amino-PPO-DSPE (compound XIX), prepared as described in Example 4A above, and the coupling agent dicyclohexylcarbodiimide (DCC, compound XXIV). The resulting reaction mixture is stirred overnight at room temperature until complete disappearance of H$_2$H-PPO-DSPE is observed, as determined by TLC. The resulting copolymer-lipid surfactant product, mPEG-(3-amido-PPO-DSPE)-(4-nitrophenyl)disulfide (compound XXV) is purified by silica gel column chromatography and characterized by NMR. The modified disulfide product possesses enhanced susceptibility to cleavage of the disulfide linkage, e.g., attack by an incoming thiol such as cysteine, or glutathione.

EXAMPLE 6

Preparation of Folic Acid-PEG-DSPE

Because folic acid is light sensitive, this procedure was performed under light protected conditions. As illustrated in FIG. 12A, folic acid (compound XXVI, 25 mg 5.6×10$^{-5}$, 1.6 equiv.), amino-PEG-DSPE (compound XXVII, 97 mg, 3.4× 10$^{-5}$, 1 equiv., prepared as described in Zalipsky (1994)) and N-hydroxy-s-norbornene-2,3-dicarboxylic acid imide (HONB, 10 mg, 5.5×10$^{-5}$, 1.6 equiv.) were dissolved into DMSO (1.0 ml) and pyridine (0.5 ml).

The mixture was stirred until completely dissolved. Dicyclohexyl-carbodiimide (DCC, 32 mg, 1.5×10$^{-4}$, 4.4 equiv.) was added to initiate the reaction. The mixture was stirred at room temperature for four hours and completion of reaction to form folic acid-PEG-DSPE (compound XXVIII) was confirmed by TLC (amino-PEG-DSPE should be absent). Pyridine was then evaporated from the reacted mixture.

For the TLC, the samples were dissolved in 50 μl DMSO and diluted with 1.0 ml chloroform. The reaction mixtures were diluted with chloroform in order to dissolve folic acid. Matrix matching with DMSO maintains the RF value between samples. The TLC running solvents were:

(1) isopropyl alcohol/ammonia/water 10:1:2 (requires 40 minutes), and
(2) chloroform/methanol/water 75:30:5 (requires 14 minutes). Visualization techniques are U.V. and Dragendorff spray. The RF values and visualization techniques in TLC solvents were:

| | RF Value | | | |
|---|---|---|---|---|
| | solvent system (1) | solvent system (2) | U.V. | Dragendorff |
| Folic acid | 0.21 | 0.0 | + | − |
| NH$_2$PEG-DSPE | 0.36 | 0.84 | − | + |
| folic acid-PEG-DSPE | 0.52 | 0.59 | + | + |

EXAMPLE 7

Preparation of Pyridoxal-PEG-DSPE

Pyridoxal (compound XXIX) and hydrazide-derivatized PEG attached to DSPE (compound XXX, prepared as described in Zalipsky (1993)) are mixed at room temperature (20°–25° C.) in DMF to form the pyridoxal-PEG-DSPE conjugate (compound XXI) shown in FIG. 12B.

EXAMPLE 8

In vitro Liposome Fusion with Erythrocyte Cells

A. Preparation of Resealed Human Erythrocyte Ghosts

Human group O whole blood was drawn into a heparin-containing tube and the cells were washed three times with a 5× volumes of cold phosphate buffered saline (PBS). After the third wash the cells were resuspended to a 50% volume/volume suspension in cold PBS. The cells were lysed by slowly introducing one mL of the 50% cell suspension into 100 mL ice cold distilled water containing 5 mM Mg SO$_4$ with constant stirring. After 10 minutes, 848 mg of solid NaCl was added to the suspension to restore isotonicity. The ghosts were resealed by incubating the suspension at 37° C. for one hour. The suspension was transferred to centrifuge tubes and spun at 10,000 rpm for 30 minutes at 4° C. The pelleted "pink" erythrocyte ghosts were resuspended (5% volume/volume) in 5% glucose.

B. Preparation of Liposomes

A total of 20 mg of the lipids in the table below was dissolved in 1 mL diethyl ether in a 10 mL screw cap culture tube.

| Amount (mole %) | Lipid Component |
|---|---|
| 5 | 1,2-dioleyloxy-3-(trimethylamino) propane (DOTAP) |
| 10 | lyso phosphatidylcholine |
| 5 | mPEG-S-S-PPO-DS (Compound XII, FIG. 8) |
| 40 | cholesterol |
| 40 | partially hydrogenated soy phosphatidylcholine (IV 40–45) |

The mixture was heated slightly to dissolve the lipids and 0.3 mL of a 100 mM solution of 6-carboxyfluorescein (6-CF) in distilled water (300 mOsm) was added. The two phases were emulsified by sonication in a bath-type sonicator for 10 minutes at room temperature. The tube was placed in a evaporation sleeve and affixed to a rotary evaporator. A sufficient vacuum was applied to slowly evaporate the ether over a period of about 10 minutes. The sleeve was immersed in a water bath at 37° C. and the vacuum slowly increased. As the ether evaporated a gel formed which eventually collapsed. An additional 0.05 mL of the 6-CF solution was added and the suspension vortexed. The remaining residual ether was removed by placing the tube under high vacuum for 10 minutes. The liposomes suspension thus formed was passed over a Sephadex G-75 column (10 mm×25 cm) pre-equilibrated with solution of 5% glucose. The liposomes which eluted with the void volume of the column were collected and used without further dilution.

C. Liposome-erythrocyte Ghost Fusion Experiment 0.5 mL of the ice cold suspension of resealed erythrocyte ghosts was placed in two centrifuge tubes and 10 microliters of the liposome suspension was added to each. The liposomes bound quickly to the ghosts as evidenced by extension immediate agglutination of the ghosts. Both tubes were allowed to incubate in an ice bath for 1 hour to allow the liposomes to bind the ghosts more completely. To ensure close contact between the liposome and ghost membranes, the mixture was centrifuged at 10,000×G for 10 minutes at 4° C. Following the centrifugation step, 10 microliters of 0.1M solution of dithiothreitol (DTT) in 5% glucose was added to one tube and 10 microliters of 5% glucose to the other, as a control. The tubes were allowed to incubate for 2 hours in the refrigerator. The tubes were vortexed to resuspend the ghost cells and a 10 microliter sample of each was removed and placed on a glass microscope slide. A cover slip was over-laid on the suspension and the slides were examined under both phase contrast and fluorescence optics at a magnification of ×630. A photomicrograph of the sample exposed to DTT and observed under fluorescence optics is shown in FIG. 13. The control containing ghosts that were bound to liposomes that had not been exposed to DTT showed no evidence of liposome-cell fusion, i.e., none of the ghosts in the optical field under florescence optics exhibited internal fluorescence. In contrast, greater than about 30% of the total ghost cells that had bound liposomes and that were exposed to DTT exhibited intense internal florescence indicating the fluorescein-containing liposomes had fused with the ghost membranes.

EXAMPLE 9

In vivo Administration of Releasable PEG Liposomes

A. Liposome Formulations

Cationic liposomes having a surface coating of PEG and complexed to a luciferase-bearing plasmid were prepared as follows.

B. Preparation of Cationic Liposome/Plasmid Complex

Cationic liposomes composed of the lipids dimethyldioctadecylammonium and cholesterol (DDAB:CHOL) were prepared according to standard procedures by dissolving 10 $\mu$mole DDAB and 10 $\mu$mole CHOL in an organic solvent containing primarily $CHCl_3$. The lipid solution was dried as a thin film by rotation under reduced pressure. The lipid film was hydrated by the addition of the desired aqueous phase, e.g., water, saline or buffer, to form liposomes (at a total lipid concentration of 20 $\mu$mole/ml) which were sized by sonication or by sequential extrusion through Nucleopore polycarbonate membranes with pore sizes of 0.4 $\mu$m, 0.2 $\mu$m, 0.1 $\mu$m and 0.05 $\mu$m to obtain liposomes of 100–150 nm in size.

A luciferase plasmid was used as a report gene. The plasmid was condensed for complexing with the cationic liposomes by adding 100 $\mu$l of a solution containing 1 mg/ml total histone in an aqueous medium to 400 $\mu$l of solubilized plasmid (1 mg plasmid/ml). The condensed plasmid had an average diameter of approximately 150 nm, as measured by dynamic light scattering.

Cationic liposome/condensed plasmid complexes were prepared by adding 280 $\mu$l of the cationic liposome suspension (20 $\mu$mole/ml) to 500 $\mu$l of the histone-condensed plasmid particles. The liposome-plasmid complexes had an average diameter of about 200 nm, as measured by dynamic light scattering.

C. Insertion of PEG

Distearyl phosphatidylethanolamine (DSPE) was derivatized with PEG, as described by Zalipsky, 1992a. PEG-DSPE micelles were prepared from PEG-DSPE by dissolving 1 mM in water and sonicating.

Micelles of PEG-DTP-DSPE, that is, PEG attached to DSPE by a cleavable disulfide linkage (compound XXV, prepared as described above in Example 5), were prepared by dissolving 1 mM PEG-DTP-DSPE in water and sonicating.

Liposomes containing 2.5 mole percent of PEG-DSPE were prepared by adding 140 $\mu$l of the PEG-DSPE micelle suspension (1 $\mu$mole lipid/ml) to 5.6 $\mu$moles lipid of the cationic lipid-plasmid complexes. The micelle-complex suspension was incubated for 5 minutes at room temperature with gentle vortexing to achieve insertion of the PEG-DSPE into the cationic liposomes (Uster). This liposome formulation is indicted in FIGS. 14A–14B as "PEG".

Liposomes containing 1 mole percent of PEG-DSPE and 1 mole percent of PEG-DTP-DSPE were prepared as described above for the 2.5% PEG-DSPE liposomal composition, except the cationic liposome-plasmid complex was incubated with micelles of PEG-DSPE and PEG-DTP-DSPE to form liposomes having a surface coating of PEG chains, where half of the PEG chains were releasably attached to the liposome surface. This liposome formulation is indicted in FIGS. 14A–14B as "PEG+R-PEG".

Liposomes containing 2.5 mole percent of PEG-DTP-DSPE were prepared as described above, except the total amount of PEG included was PEG-DTP-DSPE. This liposome formulation is indicted in FIGS. 14A–14B as "R-PEG".

D. In vivo Administration

The PEG-coated cationic liposome-plasmid complexes were administered to BALB/c mice obtained from Simonsen Laboratories (Gilroy, Calif.) by injection of about 100 nmoles lipid in 0.2–0.25 ml (approximately 100 $\mu$g plasmid) into the tail veins of 3 mice. 5 minutes after administration of the liposomes, 250 $\mu$l of 100 mM cysteine was injected via tail vein into each mouse. 24 hours after injection, the mice were sacrificed and tissues (lung, liver) were collected following perfusion with heparinized PBS (4° C.) under anesthesia.

At a temperature of between 0.4° C., 0.75 ml cell lysis reagent (Promega, Madison, Wis.) was added to each tissue, and the tissue was homogenized by 1 minute at 20,000 rpm. The supernatant was removed to a microcentrifuge tube and spun at 10,000 g for 5 minutes. The supernatant was collected for luciferase and protein assays. 20 $\mu$l of each sample was measured immediately by a luminometer (100 $\mu$l of luciferin and ATP containing assay buffer, 10 second measurement). The relative light unit was normalized by the amount of protein in the extracts.

The results are shown in FIGS. 14A–14B.

EXAMPLE 9

Liposome Preparation

Fusogenic liposomes are prepared according to standard procedures by dissolving in chloroform the following lipids: 85 mole percent distearyl phosphatidylglycerol (DSPG), 10 mole percent of the copolymer-lipid conjugate prepared as described in Examples 2, 3 or 4, 1 mole percent of ligand-PEG-DSPE, prepared as described in Examples 6 or 7, and 4 mole percent cholesterol. The lipids are dried as a thin film by rotation under reduced pressure. The lipid film is hydrated by addition of an aqueous phase to form liposomes which are sized by sonication or by sequential extrusion through Nucleopore polycarbonate membranes with pore sizes of 0.4 μm, 0.2 μm, 0.1 μm and 0.5 μm to obtain liposomes of 100–150 nm in size.

EXAMPLE 11

Liposomes with Entrapped DNA Plasmid

DNA plasmid pGL3 (Promega Corporation, Madison, Wis.) is condensed with spermidine (free base, Sigma Chemical Co (St Louis, Mo.)) and then entrapped in fusogenic liposomes as follows.

A 10 mM Tris buffer solution, pH 7.5, containing 0.1 mM spermidine is prepared. To 1 ml of the buffer solution (14.52 μg spermidine), 30 μg of the plasmid is added from an aqueous solution containing 0.6 μg pGL3/μl. The plasmid-spermidine solution, containing about 2 μg plasmid/μg spermidine, is mixed to form condensed, single molecules of pGL3.

A dried lipid film is prepared as described in Example 9, and then rehydrated with the plasmid-spermidine solution to form fusogenic liposomes having entrapped, condensed pGL3 plasmid molecules.

Although the invention has been described with respect to particular embodiments, it will be apparent to those skilled in the art that various changes and modifications can be made without departing from the invention.

It is claimed:

1. A liposome composition for fusion with a target membrane, comprising
   a suspension of liposomes designed for targeting to the target membrane, where each liposome (i) contains a therapeutic agent entrapped in the liposomes, and (ii) is composed of vesicle-forming lipids, a portion of the lipids derivatized by a diblock copolymer composed of a hydrophobic polymer chain covalently bound to the lipid and a hydrophilic polymer chain, the hydrophobic and hydrophilic chains being joined by a bond effective to release the hydrophilic polymer chains in response to an existing or an induced physiologic condition, thereby exposing the hydrophobic polymer chains.

2. The composition of claim 1, wherein said releasable bond is a disulfide bond or a pH sensitive chemical linkage.

3. The composition of claim 1, wherein said hydrophilic polymer chains are composed of a hydrophilic polymer selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

4. The composition of claim 4, wherein said hydrophilic polymer chains are composed of polyethylene glycol chains having a molecular weight of between 500–10,000 daltons.

5. The composition of claim 1, wherein said hydrophobic polymer is selected from the group consisting of polypropylene oxide, polyethylene, polypropylene, polycarbonate, polystyrene, polysulfone, polyphenylene oxide and polytetramethylene ether.

6. The composition of claim 5, wherein said hydrophobic polymer is polypropylene oxide having a molecular weight of between 500–3,000 daltons.

7. The composition of claim 1, wherein said hydrophobic polymer is a linear polymer effective to cause hemolysis of red blood cells when a water-soluble triblock copolymer containing the hydrophobic polymer and hydrophilic polymer chains joined to opposite ends of the hydrophobic polymer chains by disulfide bonds is incubated with such cells, and the incubate is treated with a reducing agent.

8. The composition of claim 1, wherein said liposomes further contain a ligand attached to a distal end of the hydrophilic polymer chains, said ligand effective for ligand-specific binding to a receptor molecule on a target cell surface prior to release of the hydrophilic polymer chains.

9. The composition of claim 8, wherein said ligand is selected from the group consisting of (i) folate, where the composition is intended for treating tumor cells having cell-surface folate receptors, (ii) pyridoxyl, where the composition is intended for treating virus-infected CD4+ lymphocytes, and (iii) sialyl-Lewis$^x$, where the composition is intended for treating a region of inflammation.

10. The composition of claim 1, wherein the liposomes further include a ligand attached to the liposome surface, said ligand being effective to bind to a target cell surface receptor molecule after, but not before, release of the hydrophilic polymer chains.

11. The composition of claim 1, wherein said liposomes further contain a cationic lipid effective to impart a positive liposome-surface charge, to enhance binding of liposomes to target cells after, but not before, release of the hydrophilic polymer chains.

12. The composition of claim 1, wherein the agent entrapped in the lipid vesicles is a polynucleotide capable of expressing a selected protein, when taken up by a target cell.

13. The composition of claim 1, wherein the agent entrapped in the liposomes is an oligonucleotide or oligonucleotide analog effective for sequence-specific binding to cellular RNA or DNA.

14. The composition of claim 1, wherein the liposomes are further composed of vesicle-forming lipids having a hydrophilic polymer chain linked to a vesicle-forming lipid also via said bond.

15. A method of delivering a compound to target cells in a subject, comprising
   parenterally administering to the subject, liposomes designed for reaching the target cells via the bloodstream, each liposome (i) containing said compound in entrapped forms and (ii) composed of vesicle-forming lipids, a portion of the lipids derivatized by a diblock copolymer composed of a hydrophobic polymer chain covalently bound to the lipid and a hydrophilic polymer chain, the hydrophobic and hydrophilic chains being joined by a bond effective to release the hydrophilic polymer chains in response to an existing or an induced physiologic condition, and
   contacting the liposomes at the target cells with such a condition to release said hydrophilic chains, thereby exposing said hydrophobic polymer chains for interaction with outer cell membranes of the target cells and fusion of the liposomes with the target cells.

16. The method of claim 15, wherein said hydrophilic polymer chains are releasably attached to the liposome via a reducible chemical linkage, and said contacting includes administering to the subject a reducing agent effective to release said chains.

17. The method of claim 16, wherein said chemical linkage is a disulfide linkage and said reducing agent is selected from the group consisting of cysteine, glutathione and ascorbate.

18. The method of claim 15, wherein each of said hydrophilic polymer chains is releasably attached to the liposome via a pH sensitive chemical linkage, and said contacting includes targeting the liposomes to a site having a pH effective to release said chains.

19. The method of claim 18, wherein said liposomes have sizes between 0.03–0.40 μm for extravasation into a solid tumor.

20. The method of claim 15, wherein said liposomes further contain a ligand attached to a distal end of the hydrophilic polymer chains, said ligand effective for ligand-specific binding to a receptor molecule on a target cell surface before chemical release of the hydrophilic polymer coating.

21. The method of claim 20, wherein said ligand is selected from the group consisting of (i) folate, where the composition is intended for treating tumor cells having cell-surface folate receptors, (ii) pyridoxyl, where the composition is intended for treating virus-infected CD4+ lymphocytes, and (iii) sialyl-Lewis$^x$, where the composition is intended for treating a region of inflammation.

22. The method of claim 15, wherein the liposomes further include a ligand attached to the liposome surface, said ligand being effective to bind to a target cell surface receptor molecule after, but not before, release of the hydrophilic polymer coating.

23. The method of claim 15, wherein said liposomes further contain a cationic lipid effective to impart a positive liposome-surface charge, to enhance binding of liposomes to target cells after, but not before, release of the hydrophilic polymer coating.

24. The method of claim 15, wherein the liposomes are further composed of vesicle-forming lipids having a hydrophilic polymer chain linked to a vesicle-forming lipid also via said bond.

* * * * *